United States Patent [19]

Kamano et al.

[11] Patent Number: 5,801,121
[45] Date of Patent: Sep. 1, 1998

[54] CYCLOHEXANEDIONE DERIVATIVES AND HERBICIDE CONTAINING THEM

[75] Inventors: Hideki Kamano, Sodegaura; Ichiro Nasuno, Ichihara; Hiroshi Yamamoto, Sodegaura; Kazuyoshi Koike, Ichihara, all of Japan

[73] Assignee: Idemitsu Kosan Co., Ltd., Tokyo, Japan

[21] Appl. No.: 876,980

[22] Filed: Jun. 16, 1997

[30] Foreign Application Priority Data

Dec. 27, 1996 [JP] Japan ................. 8-349866

[51] Int. Cl.$^6$ .............. A01N 43/18; C07D 335/04
[52] U.S. Cl. .................. 504/288; 549/23
[58] Field of Search ............... 549/23; 504/288

[56] References Cited

U.S. PATENT DOCUMENTS

| | | | |
|---|---|---|---|
| 5,468,878 | 11/1995 | Nasuno et al. | 549/23 |
| 5,480,858 | 1/1996 | Sakamoto et al. | 504/288 |
| 5,563,115 | 10/1996 | Barton et al. | 504/288 |

FOREIGN PATENT DOCUMENTS

| | | |
|---|---|---|
| 0 283 261 A2 | 9/1988 | European Pat. Off. |
| 94/04524 | 3/1994 | WIPO |
| 94/08988 | 4/1994 | WIPO |

*Primary Examiner*—Deborah C. Lambkin
*Attorney, Agent, or Firm*—Frishauf, Holtz, Goodman, Langer & Chick, P.C.

[57] ABSTRACT

Cyclohexanedione derivatives which can selectively control a broad range of upland soil weeds at a low dosage without causing phytotoxicity on crops cultivated in upland fields such as corn or salts thereof, and herbicides containing the cyclohexanedione derivatives and/or salts thereof as active ingredients, the cyclohexanedione derivatives having the general formula (I),

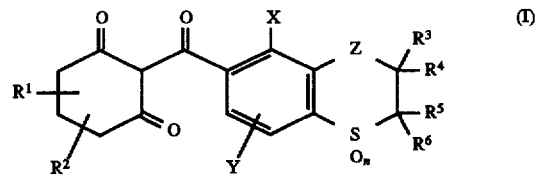

wherein symbols are as defined in the specification.

11 Claims, No Drawings

CYCLOHEXANEDIONE DERIVATIVES AND HERBICIDE CONTAINING THEM

FIELD OF THE INVENTION

The present invention relates to cyclohexanedione derivatives and herbicides containing them as active ingredients, more specifically, to cyclohexanedione derivatives which can control a broad range of upland weeds at a low dosage without causing phytotoxicity on crops such as corn, and herbicides containing them as active ingredients.

PRIOR ART

Herbicides are very important chemicals for labor-saving of weed control working and production improvement in horticultural crops. Herbicides have been therefore aggressively studied and developed for a long time, and a variety of chemicals are now practically used. However, it is still desired to develop novel herbicides having further superior herbicidal properties, particularly herbicides which can selectively control object weeds alone at a low dosage without causing phytotoxicity on cultivated crops.

During the planting time of corn, triazine-containing herbicides such as atrazine and acid anilide-containing herbicides such as alachlor and metolachlor have been conventionally used. However, atrazine shows low efficacy to grass weeds, and on the other hand, alachlor and metolachlor show low efficacy to broad-leaved weeds. It is therefore difficult at present to control grass weeds and broad-leaved weeds together simultaneously with a single herbicide. Further, these herbicides are undesirable in view of an environmental problem due to their high dosage requirement.

In view of the above circumstances, the present inventors have developed novel cyclohexanedione derivatives having a thiochroman ring and have filed patent applications therefor (WO94/04524 and WO94/08988). Typical examples of these compounds are as follows.

Compounds described in WO94/04524

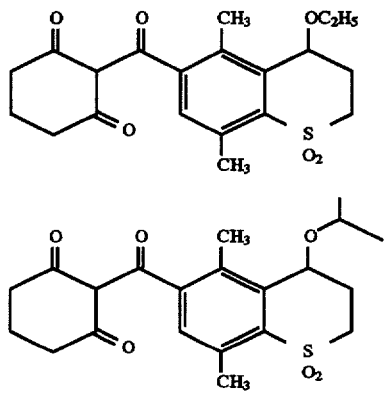

Compounds described in WO94/08988

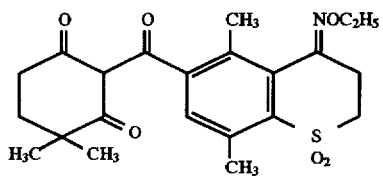

As a cyclohexanedione derivative having bicyclic properties, the following compounds have been disclosed (European Patent 0283261 A2published September, 1988).

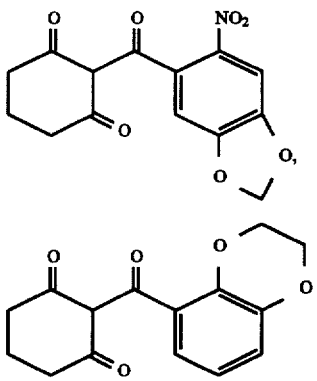

Since, however, the above compounds show phytotoxicity on sorgo and beet, it cannot be said that they have sufficient activity both in post-emergence treatment and pre-emergence treatment.

SUMMARY OF THE INVENTION

It is therefore an object of the present invention to provide a novel cyclohexanedione derivative which can control a broad range of upland weeds at a low dosage without causing phytotoxicity on crops such as corn, and a herbicide containing the same as an active ingredient.

The present inventors have made diligent studies to overcome the above problems and have found that a cyclohexanedione derivative having a specific structure can control a broad range of upland weeds at a low dosage without causing phytotoxicity on crops such as corn, and the present invention has been completed on the basis of the above finding.

According to the present invention, the above object and advantages of the present invention are achieved by the following cyclohexandedion derivatives. That is, according to the present invention, there are provided cyclohexanedione derivatives of the general formula (I) (to be sometimes referred to as "cyclohexandedione derivative of the present invention" hereinafter),

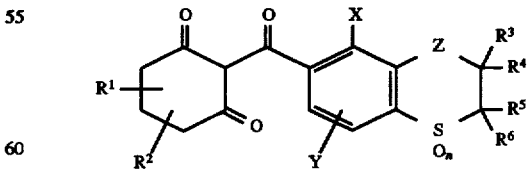

wherein each of $R^1$ and $R^2$ is independently a hydrogen atom or a $C_1$-$C_4$ alkyl group, each of $R^3$ to $R^6$ is independently a hydrogen atom, a $C_1$-$C_4$ alkyl group, a $C_1$-$C_4$ haloalkyl group or a halogen atom, n is an integer of 0, 1 or 2, X is a $C_1$-$C_4$ alkyl group, a $C_1$-$C_4$ haloakyl group, a halogen atom, a $C_1$-$C_4$ alkoxy group, a $C_1$-$C_4$ haloalkoxy group, a $C_2$-$C_4$ alkoxyalkyl group, a $C_1$-$C_4$ alkylthio group, a $C_1$-$C_4$ haloalkylthio group, a $C_1$-$C_4$ alkylsulfinyl group or a $C_1$-$C_4$ alkylsulfonyl group, Y is a hydrogen atom, a $C_1$-$C_4$ alkyl group, $C_1$-$C_4$ haloalkyl group, a halogen atom, a $C_1$-$C_4$ alkoxy group, a $C_1$-$C_4$ haloalkoxy group or a $C_2$-$C_4$ alkoxyalkyl group, and Z is a group of

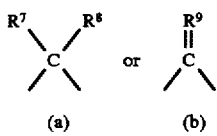

(a) (b)

in which each of $R^7$ and $R^8$ is independently a hydrogen atom, a halogen atom, a $C_1$-$C_4$ alkyl group, a $C_1$-$C_4$ alkoxy group, a $C_1$-$C_4$ alkylthio group or a group of —$NR^{10}R^{11}$, provided that when $R^7$ and/or $R^8$ are/is $C_1$-$C_4$ alkyl, $C_1$-$C_4$ alkoxy or $C_1$-$C_4$ alkylthio group (s), 1 to 9 hydrogen atoms may be substituted with 1 to 9 halogen atoms and that when the carbon number thereof is $C_2$-$C_4$, the group(s) may contain an unsaturated bond, each of $R^{10}$ and $R^{11}$ is a hydrogen atom, a $C_1$-$C_4$ alkyl group or a $C_1$-$C_4$ alkylcarbonyl group, further provided that when both $R^7$ and $R^8$ are $C_1$-$C_4$ alkyl groups, $C_1$-$C_4$ alkoxy groups or $C_1$-$C_4$ alkylthio groups, carbon atoms of $R^7$ and $R^8$ may bond to each other to form a 3- to 7-membered ring, provided that when both $R^7$ and $R^8$ are alkyl groups, compounds of the general formula (I) in which X is a $C_1$-$C_4$ alkyl group, a halogen atom or a haloalkyl group and all of $R^3$, $R^4$, $R^5$ and $R^6$ are hydrogen atoms are excluded, provided that when one of $R^7$ and $R^8$ is an alkoxy group and when the other is a hydrogen atom, compounds of the general formula (I) in which X is a $C_1$-$C_4$ alkyl group and all of $R^3$, $R^4$, $R^5$ and $R^6$ are hydrogen atoms when no hydrogen atom of the alkoxy group is replaced with halogen or when the alkoxy group contains no unsaturated bond are excluded, and $R^9$ is an oxygen atom, a sulfur atom or a $C_1$-$C_4$ alkoxyimino group, provided that when $R^9$ is a $C_1$-$C_4$ alkoxyimino group, 1 to 9 hydrogen atoms thereof may be replaced with 1 to 9 halogen atoms and that when the carbon number of $R^9$ is $C_2$-$C_4$, the $C_2$-$C_4$ alkoxyimino group may contain an unsaturated bond, and provided that compounds of the general formula (I) in which X is a $C_1$-$C_4$ alkyl group and all of $R^3$, $R^4$, $R^5$ and $R^6$ are hydrogen atoms when $R^9$ is an alkoxyimino group and when no hydrogen atom thereof is replaced with a halogen or the alkoxyimino group contains no unsaturated bond are excluded, or salt thereof.

According to the present invention, further, there are provided cyclohexanedione derivatives of the general formula (I-a1),

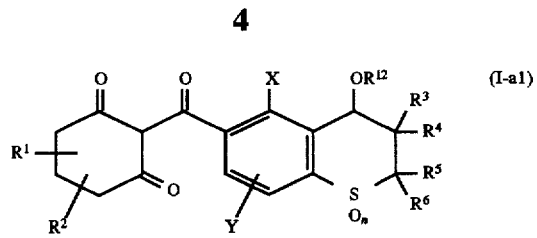

wherein $R^1$ to $R^6$, n, X and Y are as defined above, and $R^{12}$ is a $C_1$-$C_4$ alkyl group or a $C_1$-$C_4$ haloalkyl group, provided that compounds of the general formula (I-a1) in which X is a $C_1$-$C_4$ alkyl group and all of $R^3$, $R^4$, $R^5$ and $R^6$ are hydrogen atoms when $R^{12}$ is a $C_1$-$C_4$ alkyl group are excluded, or salts thereof.

According to the present invention, further, there are provided cyclohexanedione derivatives of the general formula (I-a2),

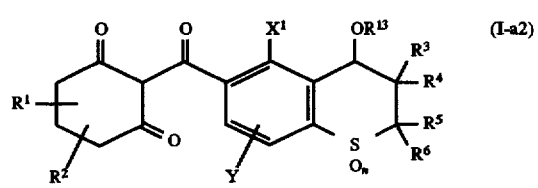

wherein $R^1$ to $R^6$, n and Y are as defined above, $R^{13}$ is a $C_1$-$C_4$ alkyl group, and $X^1$ is a $C_1$-$C_4$ haloalkyl group, a halogen atom, a $C_1$-$C_4$ alkoxy group, a $C_1$-$C_4$ haloalkoxy group, a $C_2$-$C_4$ alkoxyalkyl group, a $C_1$-$C_4$ alkylthio group, a $C_1$-$C_4$ haloalkylthio group, a $C_1$-$C_4$ alkylsulfinyl group or a $C_1$-$C_4$ alkylsulfonyl group, or salts thereof.

According to the present invention, further, there are provided cyclohexanedione derivatives of the general formula (I-a3),

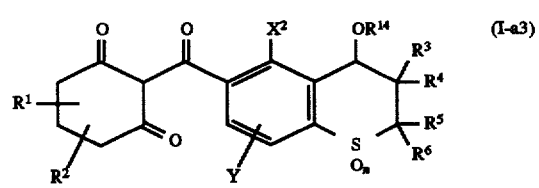

wherein $R^1$ to $R^6$, n and Y are as defined above, $R^{14}$ is a $C_1$-$C_4$ haloalkyl group, and $X^2$ is a $C_1$-$C_4$ alkyl group, a $C_1$-$C_4$ haloalkyl group, a halogen atom, a $C_1$-$C_4$ alkoxy group, a $C_1$-$C_4$ haloalkoxy group, a $C_2$-$C_4$ alkoxyalkyl group, a $C_1$-$C_4$ alkylthio group, a $C_1$-$C_4$ haloalkylthio group, a $C_1$-$C_4$ alkylsulfinyl group or a $C_1$-$C_4$ alkylsulfonyl group, and or salts thereof.

According to the present invention, further, there are provided cyclohexanedione derivatives of the general formula (I-b1),

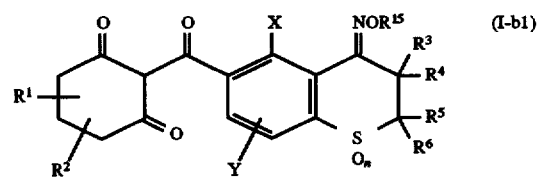

wherein $R^1$ to $R^6$, n, X and Y are as defined above, $R^{15}$ is a $C_1$–$C_4$ alkyl group or a $C_2$–$C_4$ alkenyl group, provided that compounds of the general formula (I-b1) in which X is a $C_1$–$C_4$ alkyl group and all of $R^3$, $R^4$, $R^5$ and $R^6$ are hydrogen atoms when $R^{15}$ is a $C_1$–$C_4$ alkyl group are excluded, or salts thereof.

According to the present invention, further, there are provided cyclohexanedione derivatives of the general formula (I-b2),

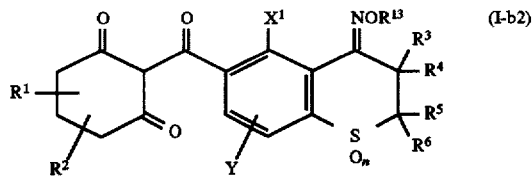

wherein $R^1$ to $R^6$, $R^{13}$, n, $X^1$ and Y are as defined above, or salts thereof.

According to the present invention, further, there are provided cyclohexanedione derivatives of the general formula (I-c),

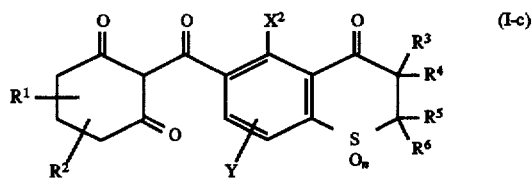

wherein $R^1$ to $R^6$, n, $X^2$ and Y are as defined above, or salts thereof.

Further, the above object and advantages of the present invention are achieved by a herbicide (to be sometimes referred to as "herbicide of the present invention" hereinafter) containing, as active ingredient, at least one of the cyclohexanedione derivatives of the above general formulae (I), (I-a1), (I-a2), (I-a3), (I-b1), (I-b2) and (I-c) and salts thereof.

DETAILED DESCRIPTION OF THE INVENTION

The cyclohexanedione derivative of the present invention will be explained first.

The cyclohexanedione derivative of the present invention has the general formula (I).

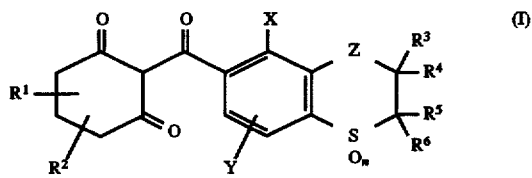

In the general formula (I), X is a $C_1$–$C_4$ alkyl group, a $C_1$–$C_4$ haloalkyl group, a halogen atom, a $C_1$–$C_4$ alkoxy group, a $C_1$–$C_4$ haloalkoxy group, a $C_2$–$C_4$ alkoxyalkyl group, a $C_1$–$C_4$ alkylthio group, a $C_1$–$C_4$ haloalkylthio group, a $C_1$–$C_4$ alkylsulfinyl group or a $C_1$–$C_4$ alkylsulfonyl group.

Examples of the above $C_1$–$C_4$ alkyl group include methyl, ethyl, propyl and butyl, and the propyl and butyl may be linear, cyclic or branched. The $C_1$–$C_4$ haloalkyl group is a group formed by replacing 1 to 9 hydrogen atoms of the above $C_1$–$C_4$ alkyl group with 1 to 9 halogen atoms (e.g., chlorine, fluorine, bromine and iodine). Specific examples thereof include —$CF_3$, —$C_2F_5$, —$C_2H_4F$, —$CH_2Cl$, —$CHF_2$, —$CCl_3$, —$C_2H_3Cl_2$, —$C_2H_3F_2$, —$C_2H_2F_3$, —$C_2H_2Cl_3$, —$C_3H_6F$, —$C_4H_8F$, —$CH_2Br$, —$CH_2I$, —$C_3H_4F_3$ and —$C_4H6F_3$. The halogen atom includes chlorine, fluorine, bromine and iodine.

Specific examples of the $C_1$–$C_4$ alkoxy group include methoxy, ethoxy, propoxy and butoxy, and the propoxy and butoxy may be linear, cyclic or branched. The $C_1$–$C_4$ haloalkoxy group is a group formed by replacing 1 to 9 hydrogen atoms of the above $C_1$–$C_4$ alkoxy group with 1 to 9 halogen atoms (e.g., chlorine, fluorine, bromine and iodine). Examples thereof include —$OCF_3$, —$OC_2F_5$, —$OC_2H_4F$, —$OC_2H_4Cl$, —$OCHF_2$, —$OCH_2F$, —$OCCl_3$, —$OC_2H_3Cl_2$, —$OC_2H_3F_2$, —$OCH_2Br$ and —$OCH_2I$.

The $C_2$–$C_4$ alkoxyalkyl group is a group formed by replacing one hydrogen atom of the above alkyl group with a $C_1$–$C_3$ alkoxy group (methoxy, ethoxy, n-propoxy or i-propoxy) Specific examples thereof include —$CH_2OCH_3$, —$CH_2OC_2H_5$, —$CH_2OC_3H_7$, —$C(CH_3)_2OCH_3$, —$CH_2CH_2OCH_3$, —$CH_2CH_2OC_2H_5$, —$CH_2(CH_2)_2OCH_3$, and —$CH_2CH_2CH_2OCH_3$.

Specific examples of the $C_1$–$C_4$ alkylthio group include methylthio, ethylthio, propylthio and butylthio, and the propylthio and butylthio may be linear, cyclic or branched. The $C_1$–$C_4$ haloalkylthio group is a group formed by replacing 1 to 9 hydrogen atoms of the above $C_1$–$C_4$ alkylthio group with 1 to 9 halogen atoms (e.g., chlorine, fluorine, bromine and iodine). Examples thereof include —$SCF_3$, —$SC_2F_5$, —$SC_2H_4F$, —$SC_2H_4Cl$, —$SCHF_2$, —$SCH_2F$, —$SCCl_3$, —$SC_2H_3Cl_2$, —$SC_2H_3F_2$, —$SCH_2Br$ and —$SCH_2I$.

Specific examples of the $C_1$–$C_4$ alkylsulfinyl group include methylsulfinyl, ethylsulfinyl, propylsulfinyl and butylsulfinyl, and the propylsulfinyl and butylsulfinyl may be linear, cyclic or branched. Examples of the $C_1$–$C_4$ alkylsulfonyl group include methylsulfonyl, ethylsulfonyl, propylsulfonyl and butylsulfonyl, and the propylsulfonyl and butylsulfonyl may be linear, cyclic or branched.

X is preferably a $C_1$–$C_4$ alkyl group, a $C_1$–$C_4$ haloakyl group or a halogen atom, more preferably methyl, chlorine or —$CF_3$, particularly preferably chlorine.

Y is a hydrogen atom, a $C_1$–$C_4$ alkyl group, a $C_1$–$C_4$ haloalkyl group, a halogen atom, a $C_1$–$C_4$ alkoxy group, a $C_1$–$C_4$ haloalkoxy group or a $C_2$–$C_4$ alkoxyalkyl group.

The above $C_1$–$C_4$ alkyl group, $C_1$–$C_4$ haloalkyl group, halogen atom, $C_1$–$C_4$ alkoxy group, $C_1$–$C_4$ haloalkoxy group or $C_2$–$C_4$ alkoxyalkyl group includes those specified with regard to the above X. The position of the substituent Y is the 7- or 8-position of the thiochroman ring, particularly preferably the 8-position. Y is preferably a hydrogen atom, a $C_1$–$C_4$ alkyl group or a halogen atom, particularly preferably hydrogen, methyl or chlorine.

Each of $R^1$ and $R^2$ is independently a hydrogen atom or a $C_1$–$C_4$ alkyl group, and each of $R^3$, $R^4$, $R^5$ and $R^6$ is independently a hydrogen atom, a $C_1$–$C_4$ alkyl group, a $C_1$–$C_4$ haloalkyl group or a halogen atom. Specific examples of the above $C_1$–$C_4$ alkyl groups, $C_1$–$C_4$ haloalkyl group and halogen atom are those specified with regard to X.

Each of $R^3$, $R^4$, $R^5$ and $R^6$ is independently preferably a hydrogen atom or a $C_1$–$C_4$ alkyl group such as methyl, particularly preferably a hydrogen atom or methyl.

n refers to the number of oxygen atom(s) bonding to the sulfur atom of the thiochroman ring, and it is 0 (sulfide), 1 (sulfoxide) or 2 (sulfone), preferably 0 (sulfide) or 2 (sulfone).

Z is a group of

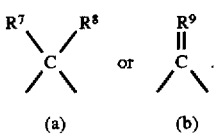

In the group (a) in the definition of Z, each of $R^7$ and $R^8$ is independently a hydrogen atom, a halogen atom, a $C_1$–$C_4$ alkyl group, a $C_1$–$C_4$ alkoxy group, a $C_1$–$C_4$ alkylthio group or a group of —$NR^{10}R^{11}$. When $R^7$ and/or $R^8$ are/is $C_1$–$C_4$ alkyl, $C_1$–$C_4$ alkoxy or $C_1$–$C_4$ alkylthio group(s), 1 to 9 hydrogen atoms of the group(s) may be replaced with 1 to 9 halogen atoms, and when the group(s) has/have 2 to 4 carbon atoms, the group(s) may contain an unsaturated bond. Each of $R^{10}$ and $R^{11}$ is a hydrogen atom, a $C_1$–$C_4$ alkyl group or a $C_1$–$C_4$ alkylcarbonyl group. Further, when both $R^7$ and $R^8$ are $C_1$–$C_4$ alkyl groups, $C_1$–$C_4$ alkoxy groups or $C_1$–$C_4$ alkylthio groups, carbon atoms of $R^7$ and $R^8$ may form a 3- to 7-membered ring by bonding to each other.

However, when $R^7$ and $R^8$ are both alkyl groups, there is excluded a case where X is a $C_1$–$C_4$ alkyl group, a halogen atom or a haloalkyl group and all of $R^3$, $R^4$, $R^5$ and $R^6$ are hydrogen atoms.

Further, when one of $R^7$ and $R^8$ is an alkoxy group and when the other is a hydrogen atom, there is excluded a case where X is a $C_1$–$C_4$ alkyl group and all of $R^3$, $R^4$, $R^5$ and $R^6$ are hydrogen atoms when no hydrogen atom is replaced with halogen or when the alkoxy group contains no unsaturated bond.

Specific examples of the halogen atom, $C_1$–$C_4$ alkyl group, $C_1$–$C_4$ alkoxy group and $C_1$–$C_4$ alkylthio group in the above $R^7$, $R^8$, $R^{10}$ and $R^{11}$ are those specified with regard to X. Examples of $C_1$–$C_4$ alkylcarbonyl group in the definition of $R^{10}$ and $R^{11}$ include acetyl, propionyl, butylyl and valeryl, and the butylyl and valeryl may be linear, cyclic or branched.

In the group (b) in the definition of Z, $R^9$ is an oxygen atom, a sulfur atom or a $C_1$–$C_4$ alkoxyimino group. When $R^9$ is a $C_1$–$C_4$ alkoxyimino group, 1 to 9 hydrogen atoms of the group may be replaced with 1 to 9 halogen atoms, and when the group has 2 to 4 carbon atoms, the group may contain an unsaturated bond. However, when $R^9$ is an alkoxyimino group, and when no hydrogen atom thereof is replaced with halogen or when the group contains no unsaturated bond, there is excluded a case where X is a $C_1$–$C_4$ alkyl group and all of $R^3$, $R^4$, $R^5$ and $R^6$ are hydrogen atoms. The alkoxyimino group is preferably methoxyimino or ethoxyimino.

Of the cyclohexanedione derivatives of the general formula (I), preferred are cyclohexanedione derivatives of the general formula (I-a1),

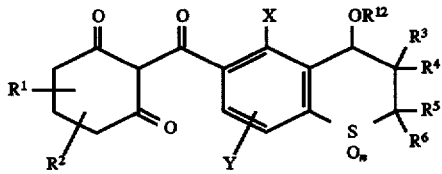

wherein $R^1$ to $R^6$, n, X and Y are as defined above, and $R^{12}$ is a $C_1$–$C_4$ alkyl group or a $C_1$–$C_4$ haloalkyl group, provided that compounds of the general formula (I-a1) in which X is a $C_1$–$C_4$ alkyl group and all of $R^3$, $R^4$, $R^5$ and $R^6$ are hydrogen atoms when $R^{12}$ is a $C_1$–$C_4$ alkyl group are excluded.

Of the above cyclohexanedione derivatives, particularly preferred are cyclohexanedione derivatives of the general formula (I-a2),

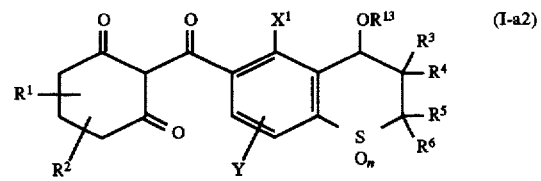

wherein $R^1$ to $R^6$, n and Y are as defined above, $R^{13}$ is a $C_1$–$C_4$ alkyl group, and $X^1$ is a $C_1$–$C_4$ haloalkyl group, a halogen atom, a $C_1$–$C_4$ alkoxy group, a $C_1$–$C_4$ haloalkoxy group, a $C_2$–$C_4$ alkoxyalkyl group, a $C_1$–$C_4$ alkylthio group, a $C_1$–$C_4$ haloalkylthio group, a $C_1$–$C_4$ alkylsulfinyl group or a $C_1$–$C_4$ alkylsulfonyl group, and cyclohexanedione derivatives of the general formula (I-a3),

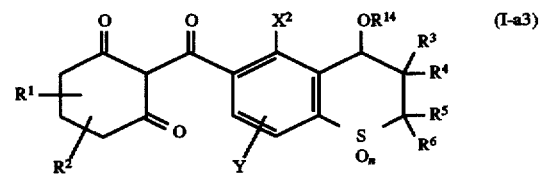

wherein $R^1$ to $R^6$, n and Y are as defined above, $R^{14}$ is a $C_1$–$C_4$ haloalkyl group, and $X^2$ is a $C_1$–$C_4$ alkyl group, a $C_1$–$C_4$ haloalkyl group, a halogen atom, a $C_1$–$C_4$ alkoxy group, a $C_1$–$C_4$ haloalkoxy group, a $C_2$–$C_4$ alkoxyalkyl group, a $C_1$–$C_4$ alkylthio group, a $C_1$–$C_4$ haloalkylthio group, a $C_1$–$C_4$ alkylsulfinyl group or a $C_1$–$C_4$ alkylsulfonyl group.

Further, preferred are cyclohexanedione derivatives of the general formula (I-b1),

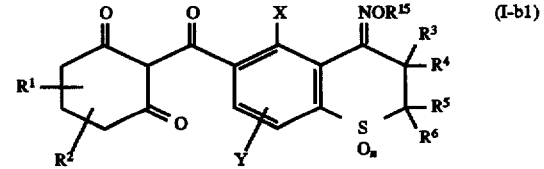

wherein $R^1$ to $R^6$, n, X and Y are as defined above, $R^{15}$ is a $C_1$–$C_4$ alkyl group or a $C_2$–$C_4$ alkenyl group, provided that when $R^{15}$ is a $C_1$–$C_4$ alkyl group, there is excluded a case where is X is a $C_1$–$C_4$ alkyl group and all of $R^3$, $R^4$, $R^5$ and $R^6$ are hydrogen atoms.

Of the above cyclohexanedione derivatives, particularly preferred are cyclohexanedione derivatives of the general formula (I-b2),

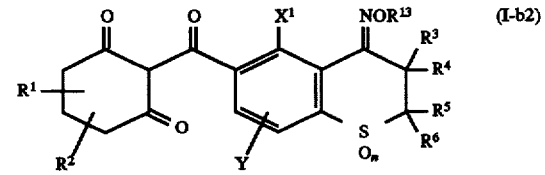

wherein $R^1$ to $R^6$, $R^{13}$, n, $X^1$ and Y are as defined above.

Further, preferred are also cyclohexanedione derivatives of the general formula (I-c),

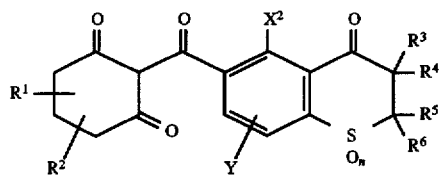

wherein $R^1$ to $R^6$, n, $X^2$ and Y are as defined above.

The cyclohexanedione derivatives of the general formula (I) can have the following structures of tautomerism, and the cyclohexanedione derivative of the present invention includes all the compounds having these structures and mixtures of these.

to salts by treating them with a base. The cyclohexanedione derivative of the present invention includes these salts.

The above base can be selected from known bases without any limitation, and examples of the base include organic bases such as amines and anilines and inorganic bases such as sodium compounds and potassium compounds. Examples of the amines include alkylamines such as monoalkylamine, dialkylamine and trialkylamine. Alkyl groups of the alkylamines are generally $C_1$–$C_4$ alkyl groups. Examples of the anilines include aniline and alkylanilines such as monoalkylaniline and dialkylaniline. Alkyl groups of the alkylanilines are generally $C_1$–$C_4$ alkyl groups. Examples of the sodium compounds include sodium hydroxide and sodium carbon-

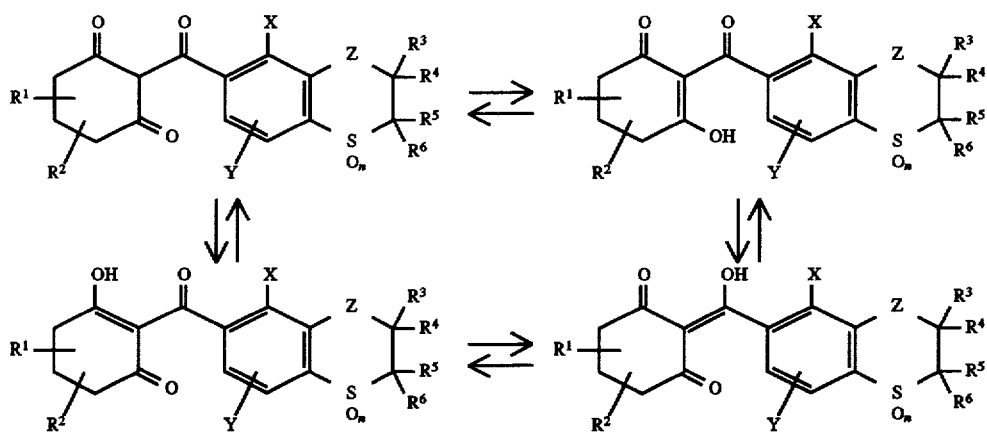

wherein X, Y, Z, $R^1$, $R^2$, $R^3$, $R^4$, $R^5$, $R^6$ and n are as defined above.

Further, the cyclohexanedione derivatives of the general formula (I) are acidic materials, and can be easily converted ate. Examples of the potassium compounds include potassium hydroxide and potassium carbonate.

The cyclohexanedione derivatives of the general formula (I) can be produced, for example, by the following method.

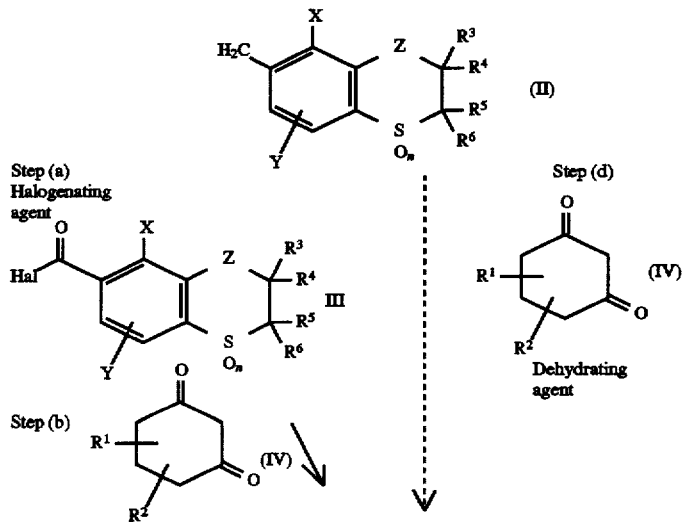

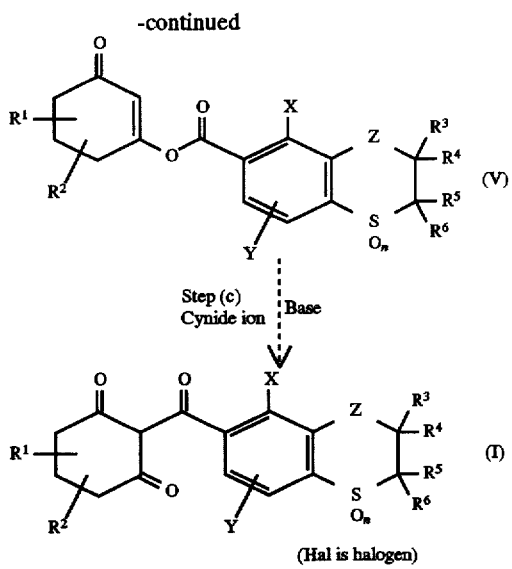

(Hal is halogen)

wherein X, Y, Z, $R^1$, $R^2$, $R^3$, $R^4$, $R^5$, $R^6$ and n are as defined above.

That is, Compound of the general formula (II) is reacted with a halogenating agent to obtain Compound of the general formula (III), and then the Compound of the general formula (III) is reacted with Compound of the general formula (IV) to obtain Compound of the general formula (V). Then, the Compound of the general formula (V) is subjected to a rearrangement reaction to obtain Cyclohexanedione derivative of the general formula (I).

Further, Compound of the general formula (V) can be obtained by reacting Compound of the general formula (II) with Compound of the general formula (IV) in the presence of a dehydrating agent such as dicyclohexylcarbodiimide (to be referred to as "DCC" hereinafter).

Each step will be explained hereinafter.

Step (a)

In step (a), Compound of the general formula (II) is reacted with a halogenating agent (thionyl chloride or phosphorus oxychloride) to obtain Compound of the general formula (III). In step (a), preferably, a halogenating agent is used in an amount of 1 mol or more per mole of Compound of the general formula (II). The reaction may be carried out in a diluted state in an inert solvent (methylene chloride or chloroform) or without any solvent. Further, an excess of thionyl chloride as a halogenating agent may be used to work it as a solvent. Although not specially limited, the reaction temperature is preferably 0° C. to the boiling point of the solvent, particularly preferably a temperature of 60° C. or around it.

Step (b)

In step (b), Compound of the general formula (III) obtained in step (a) is reacted with Compound of the general formula (IV) to obtain Compound of the general formula (V). In step (b), preferably, the molar ratio of Compound of the general formula (III)/Compound of the general formula (IV) is preferably approximately 1/1 to 1/3, and the reaction is carried out in an inert solvent such as dioxane, acetonitrile, benzene, toluene, chloroform, methylene chloride or 1,2-dichloroethane. Further, the reaction may be carried out in a solvent of two-phase system such as water-benzene, water-toluene or water-chloroform. When a base such as sodium hydroxide, potassium hydroxide, sodium carbonate, potassium carbonate, triethylamine or pyridine is present in an equimolar amount or more, the reaction proceeds smoothly. The reaction temperature is preferably 0° C. to 60° C., particularly preferably in the range of from 0° C. to room temperature.

Step (c)

In step (c), Compound of the general formula (V) obtained in step (b) is subjected to a rearrangement reaction to obtain Cyclohexanedione derivative of the general formula (I). In step (c), preferably, the reaction is carried out in an inert solvent such as methylene chloride, 1,2-dichloroethane, toluene, acetonitrile, N,N-dimethylformamide or ethyl acetate. Acetonitrile is particularly preferred. In step (c), a proper base (sodium carbonate, potassium carbonate, triethylamine or pyridine) is used in an amount of, generally, 1 to 4 equivalent weights, preferably 1 to 2 equivalent weight, per equivalent weight of Compound of the general formula (V). In this case, the reaction smoothly proceeds in the catalytic presence of hydrogen cyanide or a compound which can generate cyanide anion in the reaction system, a so-called "cyanide source". The cyanide source is selected, for example, from metal cyanides such as sodium cyanide and potassium cyanide and cyanhydrin compounds of lower alkyl ($C_3$–$C_6$) ketones such as acetonecyanhydrin and methylisopropylketonecyanhydrin. When the metal cyanide is used, the reaction can be smoothly proceeded with by adding a phase transfer catalyst such as a crown ether during the reaction. The amount of the cyanide source per mole of Compound of the general formula (V) is generally 0.01 to 0.5 mol, preferably 0.05 to 0.2 mol. The reaction temperature is preferably 0° to 80° C. particularly preferably 20° to 40° C.

Step (d)

Step (d) shows a method for obtaining Compound of the general formula (V), which method is different from the above method. That is, in step (d), Compound (V) is obtained from Compound (II) and Compound (IV) by condensation in the presence of a dehydrating agent such as DCC. Although not specially limited, the reaction solvent used for the above condensation is preferably selected from acetonitrile, a tertiary amine or an alcohol. The reaction temperature is not specially limited so long as it is in the range of from 0° C. to the boiling point of the solvent, while the reaction temperature is preferably room temperature. The dehydrating agent can be selected from the above DCC or other agent such as 1,1-carbonyldiimidazole (CDI) or 1-(3-dimethylaminopropyl)-3-ethylcarbodiimide (EDC). The amount of the dehydrating agent based on Compound is generally 1.0 to 3.0 molar equivalent, preferably 1.0 to 1.5 molar equivalent. The molar ratio of Compound (II)/Compound (IV) is generally 1/1 to 1/3, preferably 1/1 to 1/1.5. It is sufficient to carry out the condensation of Compound (II) and Compound (IV) for 1 to 48 hours, and the condensation is generally completed for about 8 hours.

Tables 1 to 19 shows preferred embodiments of the cyclohexanedione derivatives of the general formula (I) of the present invention, obtained as described above.

TABLE 1

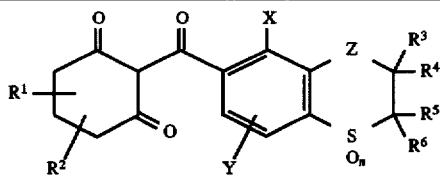

In the general formula (I)
$R^1 = R^2 = R^5 = R^6 = H$ and $n = 2$

| Comp'd No. | $R^3$ | $R^4$ | X | Y | Z |
|---|---|---|---|---|---|
| 1 | H | H | Cl | 8-F | NOCH₃ (isopropylidene) |
| 2 | H | H | Cl | 8-F | O-CH₂-F (isopropylidene) |
| 3 | H | H | Cl | 8-CH₃ | OCH₃ (isopropylidene) |
| 4 | CH₃ | CH₃ | CF₃ | 8-CH₃ | O (isopropylidene) |
| 5 | CH₃ | CH₃ | CH₃ | 8-CH₃ | O (isopropylidene) |

TABLE 2

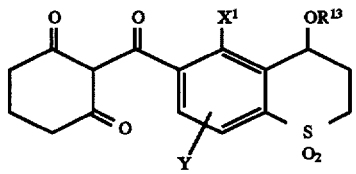

In the general formula (I-a2)
$R^1 = R^2 = R^3 = R^4 = R^5 = R^6 = H$ and $n = 2$

| Comp'd No. | $X^1$ | Y | $R^{13}$ |
|---|---|---|---|
| 6 | Cl | H | —CH₃ |
| 7 | Cl | H | —C₂H₅ |
| 8 | Cl | H | -n-C₃H₇ |
| 9 | Cl | H | -i-C₃H₇ |
| 10 | Cl | H | -s-C₄H₉ |
| 11 | Cl | H | -i-C₄H₉ |
| 12 | Cl | H | -t-C₄H₉ |
| 13 | Cl | 8-CH₃ | —C₂H₅ |
| 14 | Cl | 8-CH₃ | -n-C₃H₇ |
| 15 | Cl | 8-CH₃ | -i-C₃H₇ |
| 16 | Cl | 8-CH₃ | -s-C₄H₉ |

TABLE 2-continued

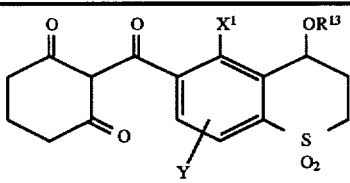

In the general formula (I-a2)
$R^1 = R^2 = R^3 = R^4 = R^5 = R^6 = H$ and $n = 2$

| Comp'd No. | $X^1$ | Y | $R^{13}$ |
|---|---|---|---|
| 17 | Cl | 8-CH₃ | -i-C₄H₉ |
| 18 | Cl | 8-CH₃ | -t-C₄H₉ |

TABLE 3

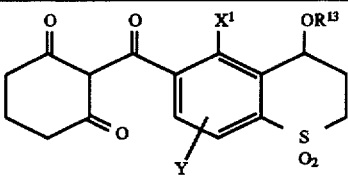

In the general formula (I-a2)
$R^1 = R^2 = R^3 = R^4 = R^5 = R^6 = H$ and $n = 2$

| Comp'd No. | $X^1$ | Y | $R^{13}$ |
|---|---|---|---|
| 19 | Cl | 8-F | —CH₃ |
| 20 | Cl | 8-F | —C₂H₅ |
| 21 | Cl | 8-F | -n-C₃H₇ |
| 22 | Cl | 8-F | -i-C₃H₇ |
| 23 | Cl | 8-F | -s-C₄H₉ |
| 24 | Cl | 8-F | -i-C₄H₉ |
| 25 | Cl | 8-F | -t-C₄H₉ |
| 26 | Cl | 8-Cl | —CH₃ |
| 27 | Cl | 8-Cl | —C₂H₅ |
| 28 | Cl | 8-Cl | -n-C₃H₇ |
| 29 | Cl | 8-Cl | -i-C₃H₇ |
| 30 | Cl | 8-Cl | -s-C₄H₉ |
| 31 | Cl | 8-Cl | -i-C₄H₉ |
| 32 | Cl | 8-Cl | -t-C₄H₉ |

TABLE 4

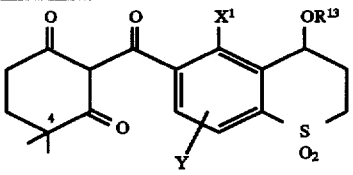

In the general formula (I-a2), each of $R^1$ and $R^2$ is methyl and bonds to the 4-position of cyclohexanedione ring, $R^3 = R^4 = R^5 = R^6 = H$, and $n = 2$.

| Comp'd No. | $X^1$ | Y | $R^{13}$ |
|---|---|---|---|
| 33 | Cl | H | —CH₃ |
| 34 | Cl | H | —C₂H₅ |
| 35 | Cl | H | -n-C₃H₇ |
| 36 | Cl | H | -i-C₃H₇ |
| 37 | Cl | H | -s-C₄H₉ |
| 38 | Cl | H | -i-C₄H₉ |
| 39 | Cl | H | -t-C₄H₉ |
| 40 | Cl | 8-CH₃ | —CH₃ |
| 41 | Cl | 8-CH₃ | —C₂H₅ |
| 42 | Cl | 8-CH₃ | -n-C₃H₇ |
| 43 | Cl | 8-CH₃ | -i-C₃H₇ |

TABLE 4-continued

In the general formula (I-a2),
each of $R^1$ and $R^2$ is methyl
and bonds to the 4-position
of cyclohexanedione ring,
$R^3 = R^4 = R^5 = R^6 = H$, and $n = 2$.

| Comp'd No. | $X^1$ | Y | $R^{13}$ |
|---|---|---|---|
| 44 | Cl | 8-CH$_3$ | -s-C$_4$H$_9$ |
| 45 | Cl | 8-CH$_3$ | -i-C$_4$H$_9$ |
| 46 | Cl | 8-CH$_3$ | -t-C$_4$H$_9$ |

TABLE 5

In the general formula (I-a2),
each of $R^1$ and $R^2$ is methyl
and bonds to the 4-position
of cyclohexanedione ring,
$R^3 = R^4 = R^5 = R^6 = H$, and $n = 2$.

| Comp'd No. | $X^1$ | Y | $R^{13}$ |
|---|---|---|---|
| 47 | Cl | 8-F | —CH$_3$ |
| 48 | Cl | 8-F | —C$_2$H$_5$ |
| 49 | Cl | 8-F | -n-C$_3$H$_7$ |
| 50 | Cl | 8-F | -i-C$_3$H$_7$ |
| 51 | Cl | 8-F | -s-C$_4$H$_9$ |
| 52 | Cl | 8-F | -i-C$_4$H$_9$ |
| 53 | Cl | 8-F | -t-C$_4$H$_9$ |
| 54 | Cl | 8-Cl | —CH$_3$ |
| 55 | Cl | 8-Cl | —C$_2$H$_5$ |
| 56 | Cl | 8-Cl | -n-C$_3$H$_7$ |
| 57 | Cl | 8-Cl | -i-C$_3$H$_7$ |
| 58 | Cl | 8-Cl | -s-C$_4$H$_9$ |
| 59 | Cl | 8-Cl | -i-C$_4$H$_9$ |
| 60 | Cl | 8-Cl | -t-C$_4$H$_9$ |

TABLE 6

In the general formula (I-a2),
each of $R^1$ and $R^2$ is methyl
and bonds to the 5-position
of cyclohexanedione ring,
$R^3 = R^4 = R^5 = R^6 = H$, and $n = 2$.

| Comp'd No. | $X^1$ | Y | $R^{13}$ |
|---|---|---|---|
| 61 | Cl | H | —CH$_3$ |
| 62 | Cl | H | —C$_2$H$_5$ |
| 63 | Cl | H | -n-C$_3$H$_7$ |
| 64 | Cl | H | -i-C$_3$H$_7$ |

TABLE 6-continued

In the general formula (I-a2),
each of $R^1$ and $R^2$ is methyl
and bonds to the 5-position
of cyclohexanedione ring,
$R^3 = R^4 = R^5 = R^6 = H$, and $n = 2$.

| Comp'd No. | $X^1$ | Y | $R^{13}$ |
|---|---|---|---|
| 65 | Cl | H | -s-C$_4$H$_9$ |
| 66 | Cl | H | -i-C$_4$H$_9$ |
| 67 | Cl | H | -t-C$_4$H$_9$ |
| 68 | Cl | 8-CH$_3$ | —CH$_3$ |
| 69 | Cl | 8-CH$_3$ | —C$_2$H$_5$ |
| 70 | Cl | 8-CH$_3$ | -n-C$_3$H$_7$ |
| 71 | Cl | 8-CH$_3$ | -i-C$_3$H$_7$ |
| 72 | Cl | 8-CH$_3$ | -s-C$_4$H$_9$ |
| 73 | Cl | 8-CH$_3$ | -i-C$_4$H$_9$ |
| 74 | Cl | 8-CH$_3$ | -t-C$_4$H$_9$ |

TABLE 7

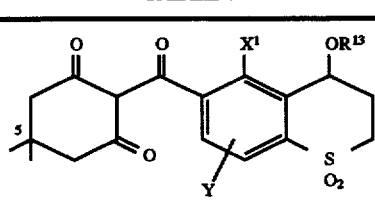

In the general formula (I-a2),
each of $R^1$ and $R^2$ is methyl
and bonds to the 5-position
of cyclohexanedione ring,
$R^3 = R^4 = R^5 = R^6 = H$, and $n = 2$.

| Comp'd No. | $X^1$ | Y | $R^{13}$ |
|---|---|---|---|
| 75 | Cl | 8-F | —CH$_3$ |
| 76 | Cl | 8-F | —C$_2$H$_5$ |
| 77 | Cl | 8-F | -n-C$_3$H$_7$ |
| 78 | Cl | 8-F | -i-C$_3$H$_7$ |
| 79 | Cl | 8-F | -s-C$_4$H$_9$ |
| 80 | Cl | 8-F | -i-C$_4$H$_9$ |
| 81 | Cl | 8-F | -t-C$_4$H$_9$ |
| 82 | Cl | 8-Cl | —CH$_3$ |
| 83 | Cl | 8-Cl | —C$_2$H$_5$ |
| 84 | Cl | 8-Cl | -n-C$_3$H$_7$ |
| 85 | Cl | 8-Cl | -i-C$_3$H$_7$ |
| 86 | Cl | 8-Cl | -s-C$_4$H$_9$ |
| 87 | Cl | 8-Cl | -i-C$_4$H$_9$ |
| 88 | Cl | 8-Cl | -t-C$_4$H$_9$ |

TABLE 8

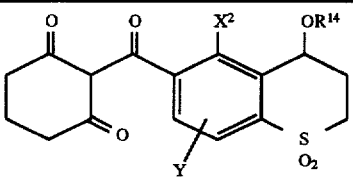

In the general formula (I-a3),
$R^1 = R^2 = R^3 = R^4 = R^5 = R^6 = H$ and $n = 2$.

| Comp'd No. | $X^1$ | Y | $R^{13}$ |
|---|---|---|---|
| 89 | $CH_3$ | H | $-CH_2CH_2F$ |
| 90 | $CH_3$ | H | $-CH_2CHF_2$ |
| 91 | $CH_3$ | H | $-CH_2CF_3$ |
| 92 | $CH_3$ | H | $-CH_2CH_2CH_2F$ |
| 93 | $CH_3$ | H | $-CH_2CH_2Cl$ |
| 94 | $CH_3$ | 8-$CH_3$ | $-CH_2CH_2F$ |
| 95 | $CH_3$ | 8-$CH_3$ | $-CH_2CHF_2$ |
| 96 | $CH_3$ | 8-$CH_3$ | $-CH_2CF_3$ |
| 97 | $CH_3$ | 8-$CH_3$ | $-CH_2CH_2CH_2F$ |
| 98 | $CH_3$ | 8-$CH_3$ | $-CH_2CH_2Cl$ |
| 99 | Cl | H | $-CH_2CH_2F$ |
| 100 | Cl | H | $-CH_2CHF_2$ |
| 101 | Cl | H | $-CH_2CF_3$ |
| 102 | Cl | H | $-CH_2CH_2CH_2F$ |
| 103 | Cl | H | $-CH_2CH_2Cl$ |

TABLE 9

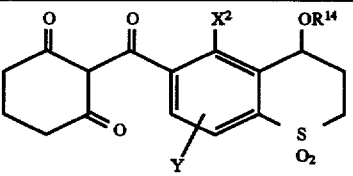

In the general formula (I-a3),
$R^1 = R^2 = R^3 = R^4 = R^5 = R^6 = H$ and $n = 2$.

| Comp'd No. | $X^1$ | Y | $R^{13}$ |
|---|---|---|---|
| 104 | Cl | 8-$CH_3$ | $-CH_2CH_2F$ |
| 105 | Cl | 8-$CH_3$ | $-CH_2CHF_2$ |
| 106 | Cl | 8-$CH_3$ | $-CH_2CF_3$ |
| 107 | Cl | 8-$CH_3$ | $-CH_2CH_2CH_2F$ |
| 108 | Cl | 8-$CH_3$ | $-CH_2CH_2Cl$ |
| 109 | Cl | 8-Cl | $-CH_2CH_2F$ |
| 110 | Cl | 8-Cl | $-CH_2CHF_2$ |
| 111 | Cl | 8-Cl | $-CH_2CF_3$ |
| 112 | Cl | 8-Cl | $-CH_2CH_2CH_2F$ |
| 113 | Cl | 8-Cl | $-CH_2CH_2Cl$ |

TABLE 10

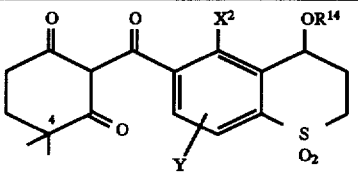

In the general formula (I-a3),
each of $R^1$ and $R^2$ is methyl and
bonds to the 4-position of
cyclohexanedione ring,
$R^3 = R^4 = R^5 = R^6 = H$ and $n = 2$.

| Comp'd No. | $X^2$ | Y | $R^{14}$ |
|---|---|---|---|
| 114 | $CH_3$ | H | $-CH_2CH_2F$ |
| 115 | $CH_3$ | H | $-CH_2CHF_2$ |

TABLE 10-continued

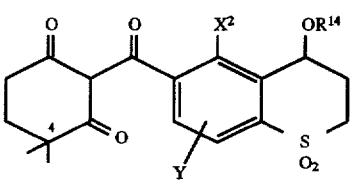

In the general formula (I-a3),
each of $R^1$ and $R^2$ is methyl and
bonds to the 4-position of
cyclohexanedione ring,
$R^3 = R^4 = R^5 = R^6 = H$ and $n = 2$.

| Comp'd No. | $X^2$ | Y | $R^{14}$ |
|---|---|---|---|
| 116 | $CH_3$ | H | $-CH_2CF_3$ |
| 117 | $CH_3$ | H | $-CH_2CH_2CH_2F$ |
| 118 | $CH_3$ | H | $-CH_2CH_2Cl$ |
| 119 | $CH_3$ | 8-$CH_3$ | $-CH_2CH_2F$ |
| 120 | $CH_3$ | 8-$CH_3$ | $-CH_2CHF_2$ |
| 121 | $CH_3$ | 8-$CH_3$ | $-CH_2CF_3$ |
| 122 | $CH_3$ | 8-$CH_3$ | $-CH_2CH_2CH_2F$ |
| 123 | $CH_3$ | 8-$CH_3$ | $-CH_2CH_2Cl$ |
| 124 | Cl | H | $-CH_2CH_2F$ |
| 125 | Cl | H | $-CH_2CHF_2$ |
| 126 | Cl | H | $-CH_2CF_3$ |
| 127 | Cl | H | $-CH_2CH_2CH_2F$ |
| 128 | Cl | H | $-CH_2CH_2Cl$ |

TABLE 11

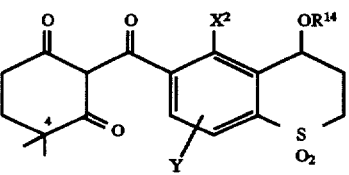

In the general formula (I-a3),
each of $R^1$ and $R^2$ is methyl and
bonds to the 4-position of
cyclohexanedione ring,
$R^3 = R^4 = R^5 = R^6 = H$ and $n = 2$.

| Comp'd No. | $X^2$ | Y | $R^{14}$ |
|---|---|---|---|
| 129 | Cl | 8-$CH_3$ | $-CH_2CH_2F$ |
| 130 | Cl | 8-$CH_3$ | $-CH_2CHF_2$ |
| 131 | Cl | 8-$CH_3$ | $-CH_2CF_3$ |
| 132 | Cl | 8-$CH_3$ | $-CH_2CH_2CH_2F$ |
| 133 | Cl | 8-$CH_3$ | $-CH_2CH_2Cl$ |
| 134 | Cl | 8-Cl | $-CH_2CH_2F$ |
| 135 | Cl | 8-Cl | $-CH_2CHF_2$ |
| 136 | Cl | 8-Cl | $-CH_2CF_3$ |
| 137 | Cl | 8-Cl | $-CH_2CH_2CH_2F$ |
| 138 | Cl | 8-Cl | $-CH_2CH_2Cl$ |

TABLE 12

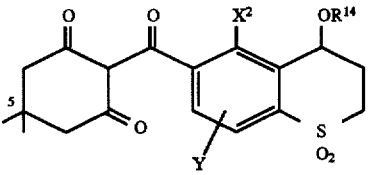

In the general formula (I-a3),
each of $R^1$ and $R^2$ is methyl and
bonds to the 5-position of
cyclohexanedione ring,
$R^3 = R^4 = R^5 = R^6 = H$ and $n = 2$.

| Comp'd No. | $X^2$ | Y | $R^{14}$ |
|---|---|---|---|
| 139 | $CH_3$ | H | $-CH_2CH_2F$ |
| 140 | $CH_3$ | H | $-CH_2CHF_2$ |
| 141 | $CH_3$ | H | $-CH_2CF_3$ |
| 142 | $CH_3$ | H | $-CH_2CH_2CH_2F$ |
| 143 | $CH_3$ | H | $-CH_2CH_2Cl$ |
| 145 | $CH_3$ | 8-$CH_3$ | $-CH_2CH_2F$ |
| 146 | $CH_3$ | 8-$CH_3$ | $-CH_2CHF_2$ |
| 147 | $CH_3$ | 8-$CH_3$ | $-CH_2CF_3$ |
| 148 | $CH_3$ | 8-$CH_3$ | $-CH_2CH_2CH_2F$ |
| 149 | $CH_3$ | 8-$CH_3$ | $-CH_2CH_2Cl$ |
| 150 | Cl | H | $-CH_2CH_2F$ |
| 151 | Cl | H | $-CH_2CHF_2$ |
| 152 | Cl | H | $-CH_2CF_3$ |
| 153 | Cl | H | $-CH_2CH_2CH_2F$ |
| 154 | Cl | H | $-CH_2CH_2Cl$ |

TABLE 13

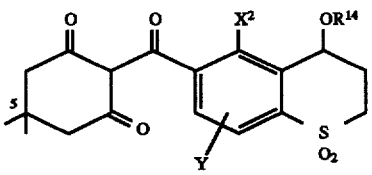

In the general formula (I-a3),
each of $R^1$ and $R^2$ is methyl and
bonds to the 5-position of
cyclohexanedione ring,
$R^3 = R^4 = R^5 = R^6 = H$ and $n = 2$.

| Comp'd No. | $X^2$ | Y | $R^{14}$ |
|---|---|---|---|
| 155 | Cl | 8-$CH_3$ | $-CH_2CH_2F$ |
| 156 | Cl | 8-$CH_3$ | $-CH_2CHF_2$ |
| 157 | Cl | 8-$CH_3$ | $-CH_2CF_3$ |
| 158 | Cl | 8-$CH_3$ | $-CH_2CH_2CH_2F$ |
| 159 | Cl | 8-$CH_3$ | $-CH_2CH_2Cl$ |
| 160 | Cl | 8-Cl | $-CH_2CH_2F$ |
| 161 | Cl | 8-Cl | $-CH_2CHF_2$ |
| 162 | Cl | 8-Cl | $-CH_2CF_3$ |

TABLE 13-continued

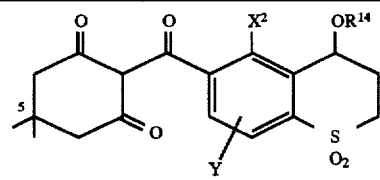

In the general formula (I-a3),
each of $R^1$ and $R^2$ is methyl and
bonds to the 5-position of
cyclohexanedione ring,
$R^3 = R^4 = R^5 = R^6 = H$ and $n = 2$.

| Comp'd No. | $X^2$ | Y | $R^{14}$ |
|---|---|---|---|
| 163 | Cl | 8-Cl | $-CH_2CH_2CH_2F$ |
| 164 | Cl | 8-Cl | $-CH_2CH_2Cl$ |

TABLE 14

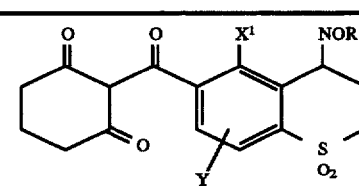

In the general formula (I-b2),
$R^1 = R^2 = R^3 = R^4 = R^5 = R^6 = H$ and $n = 2$.

| Comp'd No. | $X^1$ | Y | $R^{13}$ |
|---|---|---|---|
| 165 | Cl | H | $-CH_3$ |
| 166 | Cl | H | $-C_2H_5$ |
| 167 | Cl | H | $i\text{-}C_3H_7$ |
| 168 | Cl | 8-$CH_3$ | $-CH_3$ |
| 169 | Cl | 8-$CH_3$ | $-C_2H_5$ |
| 170 | Cl | 8-$CH_3$ | $i\text{-}C_3H_7$ |
| 171 | Cl | 8-F | $-C_2H_5$ |
| 172 | Cl | 8-F | $i\text{-}C_3H_7$ |
| 173 | Cl | 8-Cl | $-CH_3$ |
| 174 | Cl | 8-Cl | $-C_2H_5$ |
| 175 | Cl | 8-Cl | $i\text{-}C_3H_7$ |

TABLE 15

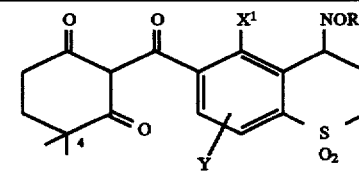

In the general formula (I-b2),
each of $R^1$ and $R^2$ is methyl and
bonds to the 4-position of
cyclohexanedione ring,
$R^3 = R^4 = R^5 = R^6 = H$ and $n = 2$.

| Comp'd No. | $X^1$ | Y | $R^{13}$ |
|---|---|---|---|
| 176 | Cl | H | $-CH_3$ |
| 177 | Cl | H | $-C_2H_5$ |
| 178 | Cl | H | $i\text{-}C_3H_7$ |
| 179 | Cl | 8-$CH_3$ | $-CH_3$ |
| 180 | Cl | 8-$CH_3$ | $-C_2H_5$ |
| 181 | Cl | 8-$CH_3$ | $i\text{-}C_3H_7$ |
| 182 | Cl | 8-F | $-CH_3$ |
| 183 | Cl | 8-F | $-C_2H_5$ |
| 184 | Cl | 8-F | $i\text{-}C_3H_7$ |
| 185 | Cl | 8-Cl | $-CH_3$ |

TABLE 15-continued

In the general formula (I-b2),
each of R¹ and R² is methyl and
bonds to the 4-position of
cyclohexanedione ring,
R³ = R⁴ = R⁵ = R⁶ = H and n = 2.

| Comp'd No. | X¹ | Y | R¹³ |
|---|---|---|---|
| 186 | Cl | 8-Cl | —C₂H₅ |
| 189 | Cl | 8-Cl | -i-C₃H₇ |

TABLE 16

In the general formula (I-b2),
each of R¹ and R² is methyl and
bonds to the 5-position of
cyclohexanedione ring,
R³ = R⁴ = R⁵ = R⁶ = H and n = 2.

| Comp'd No. | X¹ | Y | R¹³ |
|---|---|---|---|
| 190 | Cl | H | —CH₃ |
| 191 | Cl | H | —C₂H₅ |
| 192 | Cl | H | -i-C₃H₇ |
| 193 | Cl | 8-CH₃ | —CH₃ |
| 194 | Cl | 8-CH₃ | —C₂H₅ |
| 195 | Cl | 8-CH₃ | -i-C₃H₇ |
| 196 | Cl | 8-F | —CH₃ |
| 197 | Cl | 8-F | —C₂H₅ |
| 198 | Cl | 8-F | -i-C₃H₇ |
| 199 | Cl | 8-Cl | —CH₃ |
| 200 | Cl | 8-Cl | —C₂H₅ |
| 201 | Cl | 8-Cl | -i-C₃H₇ |

TABLE 17

In the general formula (I-c),
R³ = R⁴ = CH₃, R¹ = R² = R⁵ = R⁶ = H, and
n = 2.

| Comp'd No. | X² | Y |
|---|---|---|
| 202 | CH₃ | H |
| 203 | Cl | H |
| 204 | Cl | 8-CH₃ |
| 205 | Cl | 8-Cl |

TABLE 18

In the general formula (I-c),
each of R¹ and R² is methyl and
bonds to the 4-position of
cyclohexanedione ring,
R³ = R⁴ = CH₃, R⁵ = R⁶ = H and n = 2.

| Comp'd No. | X² | Y |
|---|---|---|
| 206 | CH₃ | H |
| 207 | CH₃ | 8-CH₃ |
| 208 | Cl | H |
| 209 | Cl | 8-CH₃ |
| 210 | Cl | 8-Cl |

TABLE 19

In the general formula (I-c),
each of R¹ and R² is methyl and
bonds to the 5-position of
cyclohexanedione ring,
R³ = R⁴ = CH₃, R⁵ = R⁶ = H and n = 2.

| Comp'd No. | X² | Y |
|---|---|---|
| 211 | CH₃ | H |
| 212 | CH₃ | 8-CH₃ |
| 213 | Cl | H |
| 214 | Cl | 8-CH₃ |
| 215 | Cl | 8-Cl |

In Tables 1 to 19, for example, 8-F in the column of Y means that a fluorine atom is substituted on the 8-position of the thiochroman ring.

EXAMPLES

The present invention will be explained more in detail with reference to Preparation Examples and Herbicide Examples hereinafter, while the present invention shall not be limited by these Examples.

Preparation Example 1

5-Chloro-8-fluoro-6-(1',3'-dioxocyclohexan-2-yl-carbonyl)-4-methoxyiminothiochroman-1,1-dioxide (Compound No. 1)

1-1) Synthesis of 5-chloro-8-fluoro-6-carboxyl-4-methoxyiminothiochroman-1,1-dioxide 5-Chloro-8-fluoro-6-carboxyl-4-methoxyiminothiochroman-1,1-dioxide was synthesized according to the method described in WO96/30368.

¹H-NMR (CDCl₃): δ3.35–3.45 (m,2H), 3.63–3.69 (m,2H), 4.08 (s,3H), 7.69 (d,1H)

1-2) Synthesis of 5-chloro-8-fluoro-6-(3'-oxocyclohexenyl)oxycarbonyl-4-methoxyiminothiochroman-1,1-dioxide 0.50 Gram (1.6 mmol) of 5-chloro-8-fluoro-6-carboxyl-4-methoxyiminothiochroman-1,1-dioxide was dissolved in 3 ml of dichloroethane, 0.34 ml (3.0 eq., 4.7 mmol) of thionyl chloride was added, and the mixture was refluxed under heat for 3 hours. Then, the solvent was distilled off, to give an acid chloride. Then, a solution of the obtained acid chloride in tetrahydrofuran was added to a solution of 0.18 g (1.0 eq., 1.6 mmol) of 1,3-cyclohexanedione in tetrahydrofuran, and further, 0.2 ml (1.0 eq., 1.6 mmol) of triethylamine was dropwise added. The mixture was stirred at room temperature for 2 hours, and the solvent was distilled off. The resultant residue was dissolved in ethyl acetate and consecutively washed with a 0.2N hydrochloric acid aqueous solution, with a saturated sodium hydrogencarbonate aqueous solution and with a saturated sodium chloride aqueous solution. Then, the washed product was dried over anhydrous sodium sulfate, and the solvent was distilled off. The residue was subjected to column chromatography (ethyl acetate:n-hexane=1:1) to give 0.21 g (yield 58%) of 5-chloro-8-fluoro-6-(3'-oxocyclohexenyl)oxycarbonyl-4-methoxyiminothiochroman-1,1-dioxide.

$^1$H-NMR (CDCl$_3$): δ2.0–2.7 (m,6H), 3.4–3.5 (m,4H), 4.11 (s,3H), 6.06 (bs,1H), 7.54 (d,1H)

1-3) Synthesis of 5-chloro-8-fluoro-6-(1',3'-dioxocyclohexan-2-yl-carbonyl)-4-methoxyiminothiochroman-1,1-dioxide 0.22 Gram (0.53 mmol) of 5-chloro-8-fluoro-6-(3'-oxocyclohexenyl)oxycarbonyl-4-methoxyiminothiochroman-1,1-dioxide was dissolved in 4 ml of acetonitrile, 0.1 ml (1.0 eq., 0.53 mmol) of triethylamine and 3 drops of acetonecyanhydrin were added, and the mixture was stirred at room temperature for 1 day. After the completion of the reaction, the reaction mixture was extracted with a saturated sodium hydrogencarbonate aqueous solution, and an aqueous layer was washed with methylene chloride. The aqueous layer was neutralized with 2% hydrochloric acid and extracted with ethyl acetate. An organic layer was washed with a saturated sodium chloride aqueous solution and dried over anhydrous sodium sulfate, and the solvent was distilled off to give 0.22 g (yield 100%) of 5-chloro-8-fluoro-6-(1',3'-dioxocyclohexan-2-yl-carbonyl)-4-methoxyiminothiochroman-1,1-dioxide.

$^1$H-NMR (CDCl$_3$): δ2.0–2.8 (m,7H), 3.3–3.4 (m,2H), 3.6–3.7 (m,2H), 4.05 (s,3H), 7.32 (d,1H)

IR (KBr): 2950, 1710, 1680, 1250, 1150 cm$^{-1}$

Preparation Example 2

5-Chloro-8-fluoro-6-(1',3'-dioxocyclohexan-2-yl-carbonyl)-4-(2'-fluoroethoxy)thiochroman-1,1-dioxide (Compound No. 2)

2-1) Synthesis of 5-chloro-8-fluoro-6-carboxyl-4-(2'-fluoroethoxy)thiochroman-1,1-dioxide 5-Chloro-8-fluoro-6-carboxyl-4-(2'-fluoroethoxy)thiochroman-1,1-dioxide was synthesized according to the method described in WO96/31507.

$^1$H-NMR (acetone-d$_6$): δ2.3–3.2 (m,2H), 3.3–4.5 (m,5H), 4.88 (t,1H), 5.07 (m,1H), 7.79 (d,1H)

m.p. 163°–165° C.

2-2) Synthesis of 5-chloro-8-fluoro-6-(3'-oxocyclohexenyl)oxycarbonyl-4-(2'-fluoroethoxy)thiochroman-1,1-dioxide 0.47 Gram (1.4 mmol) of 5-chloro-8-fluoro-6-carboxyl-4-(2'-fluoroethoxy)thiochroman-1,1-dioxide was dissolved in 3 ml of dichloroethane, 0.20 ml (2.0 eq., 2.8 mmol) of thionyl chloride was added, and the mixture was stirred at 40°–50° C. for 3 hours. Then, the solvent was distilled off to give an acid chloride. Then, a solution of the obtained acid chloride in tetrahydrofuran was added to a solution of 0.17 g (1.0 eq., 1.4 mmol) of 1,3-cyclohexanedione in tetrahydrofuran, and further, 0.2 ml (1.0 eq., 1.6 mmol) of triethylamine was dropwise added. The mixture was stirred at room temperature for 2 hours, and the solvent was distilled off. The resultant residue was dissolved in ethyl acetate and consecutively washed with a 0.2N hydrochloric acid aqueous solution, with a saturated sodium hydrogencarbonate aqueous solution and with a saturated sodium chloride aqueous solution. Then, the washed product was dried over anhydrous sodium sulfate, and the solvent was distilled off. Thereafter, the residue was subjected to column chromatography (ethyl acetate:n-hexane=1:1) to give 0.50 g (yield 81%) of 5-chloro-8-fluoro-6-(3'-oxocyclohexenyl)oxycarbonyl-4-(2'-fluoroethoxy)thiochroman-1,1-dioxide.

$^1$H-NMR (CDCl$_3$): δ2.0–2.8 (m,8H), 3.0–4.3 (m,4H), 4.85 (t,1H), 4.96 (bs,1H), 6.06 (bs,1H), 7.54 (d,1H)

2-3) Synthesis of 5-chloro-8-fluoro-6-(1',3'-dioxocyclohexan-2-yl-carbonyl)-4-(2'-fluoroethoxy)-1,1-dioxide 0.50 Gram (1.1 mmol) of 5-chloro-8-fluoro-6-(3'-oxocyclohexenyl)oxycarbonyl-4-(2'-fluoroethoxy)thiochroman-1,1-dioxide was dissolved in 3ml of acetonitrile, 0.15 ml (1.0 eq., 1.1 mmol) of triethylamine and 3 drops of acetonecyanhydrin were added, and the mixture was stirred at room temperature for 1 day. After the completion of the reaction, the reaction mixture was extracted with a saturated sodium hydrogencarbonate aqueous solution, and an aqueous layer was washed with methylene chloride. The aqueous layer was neutralized with 2% hydrochloric acid and extracted with ethyl acetate. An organic layer was washed with a saturated sodium chloride aqueous solution and dried over anhydrous sodium sulfate, and the solvent was distilled off to give 0.50 g (yield 100%) of 5-chloro-8-fluoro-6-(1',3'-dioxocyclohexan-2-yl-carbonyl)-4-(2'-fluoroethoxy) thiochroman-1,1-dioxide.

$^1$H-NMR (CDCl$_3$): δ1.8–3.4 (m,8H), 3.6–4.4 (m,5H), 4.85 (t,1H), 4.98 (bs,1H), 7.36 (d,1H)

IR (KBr): 2975, 1690, 1320, 1170 cm$^{-1}$

Preparation Example 3

5-Chloro-8-methyl-6-(1',3'-dioxocyclohexan-2-yl-carbonyl)-4-methoxythiochroman-1,1-dioxide (Compound No. 3)

3-1) Synthesis of 5-chloro-8-methyl-6-carboxyl-4-methoxythiochroman-1,1-dioxide

5-Chloro-8-methyl-6-carboxyl-4-methoxythiochroman-1,1-dioxide was synthesized according to the method described in WO93/18031.

$^1$H-NMR (acetone-d$_6$): δ2.4–4.0 (m,4H), 2.73 (s,3H), 3.52 (s,3H), 4.85 (t,1H), 7.72 (d,1H)

3-2) Synthesis of 5-chloro-8-methyl-6-(3'-oxocyclohexenyl)oxycarbonyl-4-methoxythiochroman-1,1-dioxide 0.84 Gram (2.8 mmol) of 5-chloro-8-methyl-6-carboxyl-4-methoxythiochroman-1,1-dioxide was dissolved in 6.7 ml of t-amyl alcohol, 0.34 g (1.1 eq., 3.0 mmol) of 1,3-cyclohexanedione and 0.63 g (1.1. eq., 3.0 mmol) of N,N-dicyclohexylcarbodiimide were added, and the mixture was stirred at room temperature for 3 hours. Then, the solvent was distilled off, ethyl acetate and water were added, and an insoluble substance was removed by filtration. Then, an organic layer was washed with a saturated sodium hydrogencarbonate aqueous solution and with a saturated sodium chloride aqueous solution. Then, the washed product was dried over anhydrous sodium sulfate, and the solvent was distilled off. The residue was subjected to column chromatography (ethyl acetate:n-hexane=1:1) to give 0.40 g (yield 36%) of 5-chloro-8-methyl-6-(3'-oxocyclohexenyl)oxycarbonyl-4-methoxythiochroman-1,1-dioxide.

$^1$H-NMR (CDCl$_3$): δ2.0–2.8 (m,9H), 2.78 (s,3H), 3.0–3.4 (m,1H), 3.49 (s,3H), 3.6–4.2 (m,1H), 4.81 (t,1H), 6.07 (bs,1H), 7.69 (s,1H)

3-3) Synthesis of 5-chloro-8-methyl-6-(1',3'-dioxocyclohexan-2-yl-carbonyl)-4-methoxythiochroman-1,1-dioxide 0.40 Gram (1.0 mmol) of 5-chloro-8-methyl-6-(3'-oxocyclohexenyl)oxycarbonyl-4-methoxythiochroman-1,1-dioxide was dissolved in 2.4 ml of acetonitrile, 0.14 ml (1.0 eq., 1.0 mmol) of triethylamine and 3 drops of acetonecyanhydrin were added, and the mixture was stirred at room temperature for 8 hours. After the completion of the reaction, the reaction mixture was extracted with a sodium carbonate aqueous solution, and an aqueous layer was washed with ethyl acetate. The aqueous layer was adjusted to a pH of 1 with 5% hydrochloric acid and then extracted with ethyl acetate. An organic layer was washed with a saturated sodium chloride aqueous solution and dried over anhydrous sodium sulfate, and the solvent was distilled off to give 0.26 g (yield 65%) of 5-chloro-8-methyl-6-(1',3'-dioxocyclohexan-2-yl-carbonyl)-4-methoxythiochroman-1,1-dioxide.

$^1$H-NMR (CDCl$_3$): δ2.0–2.8 (m,9H), 2.80 (s,3H), 3.0–3.4 (m,1H), 3.46 (s,3H), 3.6–4.1 (m,1H), 4.72 (t,1H), 7.06 (s,1H)

IR (KBr): 2950, 1690, 1300, 1145 cm$^{-1}$

Preparation Example 4

5-Trifluoromethyl-3,3,8-trimethyl-6-(1',3'-dioxocyclohexan-2-yl-carbonyl)-thiochroman-4-one-1,1-dioxide (Compound No. 4)

4-1) Synthesis of 5-trifluoromethyl-3,3,8-trimethyl-6-carboxyl-thiochroman-4-one-1,1-dioxide 5-Trifluoromethyl-3,3,8-trimethyl-6-carboxyl-thiochroman-4-one-1,1-dioxide was synthesized according to the method of synthesizing 3,3,5,8-tetramethyl-6-carboxyl-thiochroman-4-one-1,1-dioxide described in WO96/25413.

$^1$H-NMR (CDCl$_3$): δ1.51 (s,6H), 2.82 (s,2H), 3.61 (s,2H), 7.75 (s,1H)

4-2) Synthesis of 5-trifluoromethyl-3,3,8-trimethyl-6-(3'-oxocyclohexenyl)oxycarbonylthiochroman-4-one-1,1-dioxide 0.40 Gram (1.1 mmol) of 5-trifluoromethyl-3,3,8-trimethyl-6-carboxyl-thiochroman-4-one-1,1-dioxide was dissolved in 3 ml of dichloroethane, 0.28 g (2.0 eq., 2.4 mmol) of thionyl chloride was added, and the mixture was refluxed under heat for 1.5 hours. Then, the solvent was distilled off to give an acid chloride. Then, a solution of the obtained acid chloride in tetrahydrofuran was added to a solution of 0.14 g (1.1 eq., 1.3 mmol) of 1,3-cyclohexanedione in tetrahydrofuran, and further, 0.13 g (1.1 eq., 1.3 mmol) of triethylamine was dropwise added. The mixture was stirred at room temperature for 2 hours, and then the solvent was distilled off. The resultant residue was dissolved in ethyl acetate and washed with a 0.2N hydrochloric acid aqueous solution, with a saturated sodium hydrogencarbonate aqueous solution and with a saturated sodium chloride aqueous solution. Then, the washed product was dried over anhydrous sodium sulfate, and the solvent was distilled off to give 0.29 g (yield 58%) of 5-trifluoromethyl-3,3,8-trimethyl-6-(3'-oxocyclohexenyl)oxycarbonylthiocchroman-4-one-1,1-dioxide.

$^1$H-NMR (CDCl$_3$): δ1.52 (s,6H), 2.0–2.8 (m,6H), 2.85 (s,3H), 3.61 (s,2H), 6.09 (bs,1H), 7.73 (s,1H)

4-3) Synthesis of 5-trifluoromethyl-3,3,8-trimethyl-6-(1',3'-dioxocyclohexan-2-yl-carbonyl)thiochroman-4-one-1,1-dioxide 0.29 Gram (0.65 mmol) of 5-trifluoromethyl-3,3,8-trimethyl-6-(3'-oxocyclohexenyl) oxycarbonylthiocchroman-4-one-1,1-dioxide was dissolved in 1.5 ml of acetonitrile, 0.07 g (1.1 eq., 0.69 mmol) of triethylamine and 3 drops of acetonecyanhydrin were added, and the mixture was stirred at room temperature for 1 day. After the completion of the reaction, the reaction mixture was extracted with a saturated sodium hydrogencarbonate aqueous solution, and an aqueous layer was washed with methylene chloride. The aqueous layer was neutralized with 2% hydrochloric acid and extracted with ethyl acetate. An organic layer was washed with a saturated sodium chloride aqueous solution and then dried over anhydrous sodium sulfate, and the solvent was distilled off to give 0.15 g (yield 30%) of 5-trifluoromethyl-3,3,8-trimethyl-6-(1',3'-dioxocyclohexan-2-yl-carbonyl) thiochroman-4-one-1,1-dioxide.

$^1$H-NMR (CDCl$_3$)a: δ1.51 (s,6H), 2.0–2.8 (m,7H), 2.82 (s,3H), 2.70 (s,3H), 3.58 (s,2H), 7.16 (s,1H)

IR (KBr): 3000, 1730, 1690, 1300, 1195, 1150 cm$^{-1}$

Preparation Example 5

3,3,5,8-Tetramethyl-6-(1',3'-dioxocyclohexan-2-yl-carbonyl)-thiochroman-4-one-1,1-dioxide (Compound No. 5)

5-1) Synthesis of 3,3,5,8-tetramethyl-6-carboxyl-thiochroman-4-one-1,1-dioxide 3,3,5,8-Tetramethyl-6-carboxyl-thiochroman-4-one-1,1-dioxide was synthesized according to the method described in WO96/25413.

$^1$H-NMR (CDCl$_3$): δ1.47 (s,6H), 2.58 (s,3H), 2.76 (s,3H), 3.53 (s,2H), 7.93 (s,1H)

5-2) Synthesis of 3,3,5,8-tetramethyl-6-(3'-oxocyclohexenyl)oxycarbonylthiochroman-4-one-1,1-dioxide 0.70 Gram (2.4 mmol) of 3,3,5,8-tetramethyl-6-carboxyl-thiochroman-4-one-1,1-dioxide was dissolved in 4 ml of dichloroethane, 0.56 g (2.0 eq., 4.7 mmol) of thionyl chloride was added, and the mixture was stirred at 55° C. for 1.5 hours. Then, the solvent was distilled off to give an acid chloride. Then, a solution of the obtained acid chloride in tetrahydrofuran was added to a solution of 0.29 g (2.6 mmol) of 1,3-cyclohexanedione in tetrahydrofuran, and further, 0.27 g (1.1 eq., 2.7 mmol) of triethylamine was dropwise added. The mixture was stirred at room temperature for 2 hours, and then the solvent was distilled off. The resultant residue was dissolved in ethyl acetate and consecutively washed with a 0.2N hydrochloric acid aqueous solution, with a saturated sodium hydrogencarbonate aqueous solution and with a saturated sodium chloride aqueous solution. Then, the washed product was dried over anhydrous sodium sulfate, and the solvent was distilled off to give 0.67 g (yield 68%) of 3,3,5,8-tetramethyl-6-(3'-oxocyclohexenyl) oxycarbonylthiochroman-4-one-1,1-dioxide.

$^1$H-NMR (CDCl$_3$): δ1.46 (s,6H), 2.0–2.8 (m,6H), 2.54 (s,3H), 2.76 (s,3H), 3.52 (s,2H), 6.04 (bs,1H), 7.85 (s,1H)

5-3) Synthesis of 3,3,5,8-tetramethyl-6-(1',3'-dioxocyclohexan-2-yl-carbonyl)-thiochroman-4-one-1,1-dioxide 0.63 Gram (1.6 mmol) of 3,3,5,8-tetramethyl-6-(3'-oxocyclohexenyl)oxycarbonylthiochroman-4-one-1,1-dioxide was dissolved in 3 ml of acetonitrile, 0.17 g (1.1 eq., 1.7 mmol) of triethylamine and 3 drops of acetonecyanhydrin were added, and the mixture was stirred at room temperature for 1 day. After the completion of the reaction, the reaction mixture was extracted with a saturated sodium hydrogencarbonate aqueous solution, and an aqueous layer was washed with methylene chloride. The washed aqueous layer was neutralized with 2% hydrochloric acid, and extracted with ethyl acetate. An organic layer was washed with a saturated sodium chloride aqueous solution and dried over anhydrous sodium sulfate, and the solvent was distilled off to give 0.51 g (yield 81%) of 3,3,5,8-tetramethyl-6-(1', 3'-dioxocyclohexan-2-yl-carbonyl)-thiochroman-4-one-1,1-dioxide.

$^1$H-NMR (CDCl$_3$): δ1.45 (s,6H), 2.0–3.0 (m,7H), 2.05 (s,3H), 2.70 (s,3H), 3.51 (s,2H), 7.07 (s,1H)

IR (KBr): 2975, 1700, 1680, 1260, 1195, 1125 cm$^{-1}$

Preparation Example 6

5-Chloro-8-methyl-6-(1',3'-dioxocyclohexan-2-yl-carbonyl)-4-isopropyloxythiochroman-1,1-dioxide (Compound No. 15)

6-1) Synthesis of 5-chloro-8-methyl-6-carboxyl-4-isopropyloxythiochroman-1,1-dioxide 5-Chloro-8-methyl-6-carboxyl-4-isopropyloxythiochroman-1,1-dioxide was synthesized according to the method described in WO93/18031 and WO96/30368.

$^1$H-NMR (CDCl$_3$): δ1.27 (6H,d), 2.4–2.8 (2H,m), 2.78 (3H,s), 3.1–3.4 (1H,m), 3.7–4.2 (2H,m), 5.15 (1H,m), 6.2–6.7 (1H, broad), 7.76 (1H,s)

6-2) Synthesis of 5-chloro-8-methyl-6-(1',3'-dioxocyclohexan-2-yl-carbonyl)-4-isopropyloxythiochroman-1,1-dioxide 2.0 Grams (6.0 mmol) of 5-chloro-8-methyl-6-carboxyl-4-isopropyloxythiochroman-1,1-dioxide was dissolved in mixed solvents of 6 ml of methylene chloride with 6 ml of 1,2-dichloroethane, 0.57 ml (7.8 mmol) of thionyl chloride was added, and the mixture was allowed to react at room temperature for 1.5 hours and at 60° C. for 2.5 hours. The reaction mixture was allowed to cool, and then, excessive thionyl chloride and the solvent were distilled off under reduced pressure, to obtain an acid chloride. To the obtained acid chloride was added 7 ml of methylene chloride, and the mixture was cooled to 0° C. in an ice salt bath. To the acid chloride solution was gradually added a solution of 0.74 g (6.6 mmol) of 1,3-cyclohexanedione and 0.67 g (6.6 mmol) of triethylaminein in 7 ml of methylene chloride, and after the dropwise addition, the mixture was allowed to react at room temperature overnight. The solvent was distilled off under reduced pressure, ethyl acetate was added to form a solution, and an insoluble substance was removed by filtration. The resultant ethyl acetate solution was consecutively washed with a saturated sodium bicarbonate aqueous solution and with a saturated sodium chloride aqueous solution, and dried over anhydrous sodium sulfate. The solvent was distilled off to give 2.91 g of an intermediate of the formula (V) in the form of a solid. The intermediate was used in a subsequent rearrangement reaction without any particular purification.

2.91 Grams of the above intermediate was suspended in 15 ml of acetonitrile, and 0.61 g (6.0 mmol) of triethylamine and 0.10 g (1.2 mmol) of acetonecyanhydrin were added. The mixture was allowed to react at room temperature for 1 hour and further allowed to react under heat at 40° C. for 3 hours. After the completion of the reaction, the solvent was distilled off under reduced pressure, and ethyl acetate was added to the resultant residue to form a solution. The solution was consecutively washed with 10% hydrochloric acid, with distilled water and with a saturated sodium chloride aqueous solution. The washed product was dried over anhydrous sodium sulfate and then ethyl acetate was distilled off under reduced pressure to give 1.81 g (yield 62%) of 5-chloro-8-methyl-6-(1,3-dioxocyclohexan-2-yl-carbonyl)-4-isopropyloxythiochroman-1,1-dioxide in the form of a solid.

$^1$H-NMR (CDCl$_3$): δ1.22 (6H,d), 1.9–2.2 (2H,m), 2.3–2.9 (6H,m), 2.73 (3H,s), 3.1–3.4 (1H,m), 3.7–4.3 (2H,m), 5.02 (1H,m), 7.05 (1H,s)

IR (KBr): 1130, 1310, 1690, 1740 cm$^{-1}$

Preparation Examples 7–14

Compounds of the formula (II) shown in Tables 20 and 21 were used as starting materials, and Compounds shown in Tables 22 and 23 were synthesized substantially in the same manner as in Preparation Example 6. Table 24 shows physical property values of the obtained Compounds.

TABLE 20

| Preparation Example No. | Starting material Compound of the formula (II) | NMR (ppm internal standard: TMS) |
| --- | --- | --- |
| 6 | (structure with Cl, HO$_2$C, isopropyloxy, S, O$_2$, Me) | 1.27(6H, d) 2.4–2.8(2H, m)<br>2.78(3H, s)<br>3.1–3.4(1H, m)<br>3.7–4.2(2H, m)<br>5.15(1H, m)<br>6.2–6.7(1H, broad)<br>7.76(1H, s)<br>CDCl$_3$ |
| 7 | (structure with Me, HO$_2$C, ethoxy-Cl, S, O$_2$, Me) | 2.3–2.8(2H, m)<br>2.62(3H, s), 2.78(3H, s)<br>3.1–3.5(1H, m)<br>3.5–4.3(5H, m)<br>4.76(1H, m) 5.9–6.4(1H, broad)<br>7.81(1H, s)<br>CDCl$_3$ |

TABLE 20-continued

| Preparation Example No. | Starting material Compound of the formula (II) | NMR (ppm internal standard: TMS) |
|---|---|---|
| 8 | 3-chloro-6-methyl-4-(2-fluoroethoxy)thiochroman-8-carboxylic acid 1,1-dioxide structure (HO₂C, Cl, Me, S O₂, O-CH₂CH₂-F) | 2.5–4.3(6H, m) 2.73(3H, s) 4.60(2H, dt) 5.06(1H, m) 7.74(1H, s) deuteroacetone |
| 9 | Cl, HO₂C, Me, S O₂ with O-CH₂CH₂-Cl substituent | 2.5–2.8(2H, m) 2.79(3H, s) 3.1–3.5(1H, m) 3.5–3.8(2H, m) 3.8 4.2(3H, m) 5.00(1H, m) 6.4–7.1(1H, broad) 7.80(1H, s) CDCl₃ |
| 10 | Cl, HO₂C, S O₂ with OMe substituent | 2.3–3.9(4H, m) 3.54(3H, s) 4.86(1H, m) 7.96(2H, ABq) deuteroacetone |

TABLE 21

| Preparation Example No. | Starting material Compound of the formula (II) | NMR (ppm internal standard: TMS) |
|---|---|---|
| 11 | Cl, HO₂C, Me, S O₂ with OEt substituent | 1.26(3H, t), 2.4–4.3(6H, m) 2.78(3H, s) 4.93(1H, s) 7.3–7.8(1H, braod) 7.70(1H, s) CDCl₃ |
| 12 | Cl, HO₂C, S O₂ with =NOMe substituent | 3.1–3.6(4H, m) 3.89(3H, s) 7.78(2H, ABq) deuteroacetone |
| 13 | Me, HO₂C, S O₂ with C(=O)C(Me)₂- structure | 1.50(6H, s) 2.68(3H, s) 3.49(2H, s) 7.90(1H, d) 8.22(1H, s) CDCl₃ |
| 14 | Cl, HO₂C, Me, S O₂ with O-propyl substituent | 0.93(3H, t) 1.4–1.8(2H, m) 2.3–4.0(6H, m) 2.73(3H, s) 4.96(1H, m) 7.71(1H, s) deuteroacetone |

TABLE 22

| Preparation Example No. | Compound No. | Obtained compound | Yield (%) |
|---|---|---|---|
| 6 | 15 | (structure) | 62 |
| 7 | 98 | (structure) | 86 |
| 8 | 104 | (structure) | 98 |
| 9 | 108 | (structure) | 60 |
| 10 | 6 | (structure) | 64 |

TABLE 23

| Preparation Example No. | Compound No. | Obtained compound | Yield (%) |
|---|---|---|---|
| 11 | 13 | (structure) | 63 |
| 12 | 165 | (structure) | 42 |

TABLE 23-continued

| Preparation Example No. | Compound No. | Obtained compound | Yield (%) |
|---|---|---|---|
| 13 | 202 | (structure: cyclohexanedione-C(O)-phenyl(Me)(SO2)-C(O)-CMe2-CH2-) | 83 |
| 14 | 14 | (structure: cyclohexanedione-C(O)-phenyl(Cl)(Me)(SO2)-CH(OCH2CH2CH3)-) | 62 |

TABLE 24

| Preparation Example No. | Compound No. | N.M.R. (ppm: Internal standard tetramethylsilano) | IR (KBr) (cm$^{-1}$) |
|---|---|---|---|
| 6 | 15 | 1.22(6H, d) 1.9–2.2(2H, m) 2.3–2.9(6H, m) 2.73(3H, s) 3.1–3.4(1H, m) 3.7–4.3(2H, m) 5.02(1H, m) 7.05(1H, s). (CDCl$_3$) | 1130, 1310 1690, 1740 |
| 7 | 98 | 1.9–2.2(2H, m) 2.23(3H, s) 2.3–4.1(12H, m) 2.71(3H, s) 4.67(1H, m) 6.96(1H, s) (CDCl$_3$) | 1140, 1300 1690 1750 |
| 8 | 104 | 1.9–2.2(2H, m) 2.3–4.2(10H, m) 4.55(2H, m) 4.91(1H, m) 7.07((1H, s) (CDCl$_3$) | 1140, 1290 1330 1680 |
| 9 | 108 | 1.9–2.2(2H, m) 2.3–4.3(12H, m) 2.74(3H, s) 4.90(1H, s) 7.07(1H, s) (CDCl$_3$) | 1120 1290 1680 |
| 10 | 6 | 1.9–2.2(2H, m) 2.3–3.9(8H, m) 3.49(3H, s) 4.79(1H, m) 4.79(1H, m) 7.48(1H, d), 7.87(1H, d) deutero acetone | 1140 1300 1680 |
| 11 | 13 | 1.22(3H, t) 1.9–2.3(2H, m) 2.3–4.2(10H, m) 2.73(3H, s) 4.82(1H, m) 7.05(1H, s) (CDCl$_3$) | 1130 1310 1680 |
| 12 | 165 | 1.9–2.2(2H, m) 2.3–2.6(2H, m) 2.7–3.1(2H, m) 3.3–3.7(4H, m) 4.05(3H, s) 7.46(1H, s) 7.93(1H, d) deutero acetone | 1160, 1310 1690 1740 |
| 13 | 202 | 1.48(6H, s) 1.9–2.2(2H, m) 2.35(3H, s) 2.3–2.5(2H, m) 2.7–2.9(2H, m) 3.48(2H, s) 7.32(1H, d) 7.85(1H, d) (CDCl$_3$) | 1140, 1330 1690 1750 |
| 14 | 14 | 0.91(3H, t) 1.4–1.8(2H, m) 1.9–4.2(12H, m) 2.72(3H, s) 4.80(1H, s) 7.05(1H, s) (CDCl$_3$) | 1140 1300 1690 |

Herbicide Examples (1) Preparation of herbicides

97 Parts by weight of talc (trade name: Zeaklite, supplied by Zeaklite Industry) as a carrier, 1.5 parts by weight of alkylarylsulfonic acid salt(trade name: Neoplex, supplied by Kao-Atlas K.K.) as a surfactant and 1.5 parts by weight of a nonionic and anionic surfactant (trade name: Sorpol 800A, supplied by Toho Chemical Co., Ltd.) were uniformly pulverized and mixed to prepare a carrier for a wettable powder.

90 Parts by weight of the above carrier for a wettable powder and 10 parts by weight of one of the compounds of the of the present invention were uniformly pulverized and mixed to obtain herbicides. Further, in Comparative Herbicide Examples, comparative herbicides were also prepared from the following compounds (A) to (G) in the same manner.

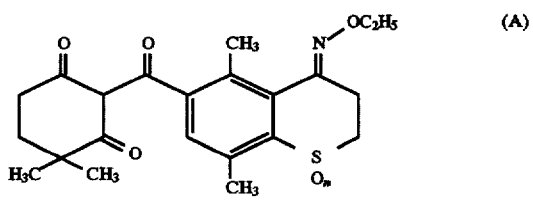

(A)

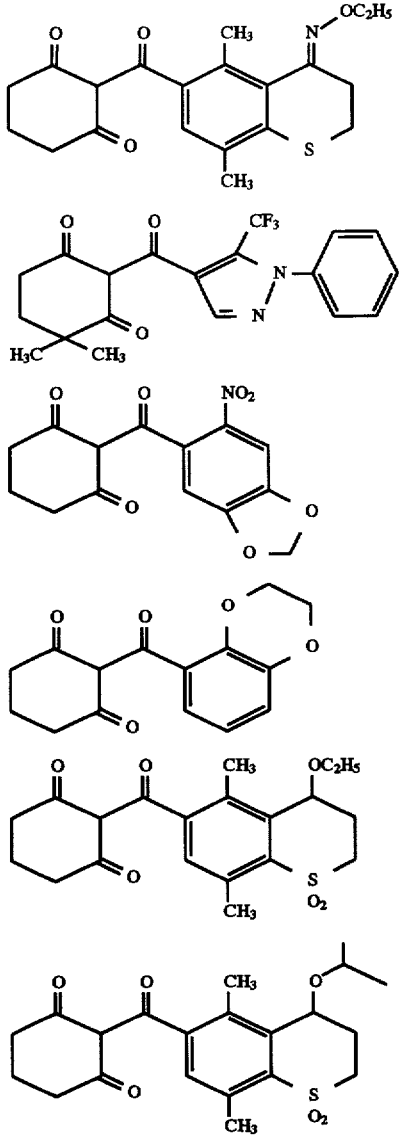

The compounds (A) and (B) are disclosed in WO94/08988, the compounds (C), (D) and (E) are disclosed in European Patent 94/283261, and the compounds (F) and (G) are disclosed in WO94/04524.

(2) Ratings of evaluation of herbicidal efficacy and phytotoxicity to crops

The ratio of remaining plant weight to plant weight in non-treated plot was determined on the basis of the ratio of remaining plant weight to plant weight in non-treated plot= (remaining plant weight in treated plot/plant weight in non-treated plot)×100. The ratings were applied to the following biological tests.

| | Ratings |
|---|---|
| | Ratio of remaining plant weight to plant weight in non-treated plot (%) |
| Herbicidal efficacy | |
| 0 | 81–100 |
| 1 | 61–80 |
| 2 | 41–60 |
| 3 | 21–40 |
| 4 | 1–20 |
| 5 | 0 |
| Phytotoxicity to crops | |
| − | 100 |
| ± | 95–99 |
| + | 90–94 |
| ++ | 80–89 |
| +++ | 0–79 |

(a) Upland pre-emergence treatment test 1

An upland pre-emergence treatment test was carried out in the following manner with regard to Compounds Nos. 1 to 5 (Examples) and Compounds (A) to (E) (Comparative Examples).

Seeds of weeds such as velvetleaf, Jimsonweed, black nightshade, barnyardgrass and large crabgrass and seeds of corn, sorgo and cotton were sown in 1/5,000-are Wagner pots filled with upland soil, and covered with upland soil. Then, a predetermined amount of the herbicide prepared in the above (1) was suspended in water and uniformly sprayed onto the soil surface. Then, the seeds were grown in a greenhouse, and on the 20th day after the treatment, the herbicide was evaluated for herbicidal efficacy and phytotoxicity to the crops on the basis of the ratings shown in (2). Table 25 shows the results.

TABLE 25

| Com'd No. | Dosage (g/ha) | Herbicidal efficacy | | | | | Phytotoxicity | | |
|---|---|---|---|---|---|---|---|---|---|
| | | AA | BB | CC | DD | EE | FF | GG | HH |
| 1 | 300 | 5 | 5 | 5 | 3 | 3 | − | − | − |
| 2 | 300 | 5 | 5 | 5 | 4 | 3 | − | − | − |
| 3 | 300 | 5 | 5 | 5 | 5 | 5 | − | − | − |
| 4 | 100 | 5 | 5 | 5 | 3 | 3 | − | − | − |
| 5 | 300 | 5 | 5 | 5 | 3 | 3 | − | − | − |
| A | 300 | 5 | 5 | 5 | 3 | 1 | − | ++ | ++ |
| B | 300 | 1 | 0 | 0 | 0 | 0 | − | − | − |
| C | 300 | 0 | 1 | 1 | 0 | 0 | − | − | − |
| D | 300 | 1 | 0 | 1 | 0 | 0 | − | − | − |
| E | 300 | 0 | 0 | 0 | 0 | 0 | − | − | − |

A = Velvetleaf, BB = Jimsonweed, CC = Black nightshade, DD = Barnyardgrass, EE = Large crabgrass, FF = Corn, GG = Sorgo, HH = Cotton Table 25 shows that the herbicides of the present invention can selectively control a broad range of upland soil weeds at a low dosage without causing phytotoxicity on corn, sorgo and cotton. In contrast, it is also shown that Compound A is poor in safety to sorgo and cotton, and that Compounds B to E are all poor in the efficacy on all the test weeds.

(b) Upland post-emergence treatment test 1

An upland post-emergence treatment test was carried out in the following manner with regard to Compounds Nos. 1 to 5 (Examples) and Compounds (A), (C), (D) and (E) (Comparative Examples).

Seeds of weeds such as cocklebur, velvetleaf, Jimsonweed, barnyardgrass and large crabgrass and seeds of corn, sorgo and beet were sown in 1/5,000-are Wagner pots filled with upland soil, and covered with upland soil. The seeds were grown in a greenhouse, and at the stage of 3–4 leaves of these plants, a predetermined amount of the herbicide prepared in the above (1) was suspended in water and uniformly sprayed onto leaf and stalk portions at a rate of 2,000 l/ha. Then, the plants were grown in the greenhouse, and on the 30th day after the treatment, the herbicide was evaluated for herbicidal efficacy and phytotoxicity to the crops on the basis of the ratings shown in (2). Table 26 shows the results.

TABLE 26

| Com'd No. | Dosage (g/ha) | Herbicidal efficacy | | | | | Phytotoxicity | | |
|---|---|---|---|---|---|---|---|---|---|
| | | AA | BB | CC | DD | EE | FF | GG | HH |
| 1 | 300 | 5 | 5 | 4 | 3 | 3 | — | — | — |
| 2 | 300 | 5 | 5 | 5 | 4 | 4 | — | — | ± |
| 3 | 300 | 5 | 5 | 3 | 3 | 3 | — | — | ± |
| 4 | 300 | 4 | 5 | 5 | 4 | 3 | — | — | ± |
| 5 | 100 | 5 | 4 | 3 | 4 | 3 | — | — | — |
| A | 300 | 5 | 5 | 5 | 4 | 0 | — | ++ | +++ |
| C | 300 | 5 | 0 | 5 | 0 | 1 | — | + | +++ |
| D | 300 | 5 | 4 | 5 | 0 | 1 | — | + | +++ |
| E | 300 | 0 | 0 | 0 | 0 | 0 | — | — | — |

AA = Cocklebur, BB = Velvetleaf, CC = Jimsonweed, DD = Barnyardgrass, EE = Large crabgrass, FF = Corn, GG = Sorgo, HH = Beet Table 26 shows that the herbicides of the present invention show no phytotoxicity on corn and sorgo, has selectivity for beet and further can selectively control a broad range of upland soil weeds at a low dosage. In contrast, it is also shown that Compounds A, C and D are poor in safety to sorgo and beet and that Compound E is poor in efficacy on all the test weeds.

(c) Upland pre-emergence treatment test 2

An upland pre-emergence treatment test was carried out in the following manner with regard to Compounds Nos. 6, 15, 104 and 165 (Examples) and Compound (F) (Comparative Example).

Seeds of weeds such as velvetleaf, black nightshade, barnyardgrass, large crabgrass and giant foxtail and seeds of corn and cotton were sown in 1/5,000-are Wagner pots filled with upland soil, and covered with upland soil. Then, a predetermined amount of the herbicide prepared in the above (1) was suspended in water and uniformly sprayed onto the soil surface. Then, the seeds were grown in a greenhouse, and on the 20th day after the treatment, the herbicide was evaluated for herbicidal efficacy and phytotoxicity to the crops on the basis of the ratings shown in (2). Table 27 shows the results.

TABLE 27

| Com'd No. | Dosage (g/ha) | Herbicidal efficacy | | | | | Phytotoxicity | |
|---|---|---|---|---|---|---|---|---|
| | | AA | BB | CC | DD | EE | FF | GG |
| 6 | 100 | 5 | 5 | 3 | 5 | 3 | — | — |
| 15 | 100 | 5 | 5 | 5 | 4 | 4 | — | — |
| 104 | 100 | 5 | 5 | 5 | 5 | 4 | — | — |
| 165 | 100 | 5 | 5 | 5 | 5 | 3 | — | — |
| F | 100 | 5 | 5 | 0 | 1 | 0 | — | — |

AA = Velvetleaf, BB = Black nightshade, CC = Barnyardgrass, DD = Large crabgrass, EE = Giant foxtail, FF = Corn, GG = Cotton Table 27 shows that the herbicides of the present invention cause no phytotoxicity on corn and cotton and can selectively control a broad range of upland soil weeds at a low dosage. In contrast, it is shown that Compound F is poor in efficacy on grass weeds.

(d) Upland post-emergence treatment test 2

An upland post-emergence treatment test was carried out in the following manner with regard to Compounds Nos. 15, 104, 165 and 202 (Examples) and Compound (F) (Comparative Example).

Seeds of weeds such as cocklebur, velvetleaf, black nightshade, barnyardgrass, large crabgrass and giant foxtail and seeds of corn and sorgo were sown in 1/5,000-are Wagner pots filled with upland soil, and covered with upland soil. The seeds were grown in a greenhouse, and at the stage of 3–4 leaves of these plants, a predetermined amount of the herbicide prepared in the above (1) was suspended in water and uniformly sprayed onto leaf and stalk portions at a rate of 2,000 l/ha. Then, the plants were grown in the greenhouse, and on the 30th day after the treatment, the herbicide was evaluated for herbicidal efficacy and phytotoxicity to the crops on the basis of the ratings shown in (2). Table 28 shows the results.

TABLE 28

| Com'd No. | Dosage (g/ha) | Herbicidal efficacy | | | | | Phytotoxicity | |
|---|---|---|---|---|---|---|---|---|
| | | AA | BB | CC | DD | EE | FF | GG | HH |
| 15 | 100 | 5 | 5 | 5 | 4 | 4 | 4 | — | — |
| 104 | 100 | 5 | 5 | 5 | 5 | 4 | 3 | — | — |
| 165 | 100 | 5 | 5 | 5 | 5 | 4 | 4 | — | — |
| 202 | 100 | 5 | 5 | 5 | 4 | 4 | 3 | — | — |
| F | 100 | 5 | 5 | 5 | 0 | 0 | 0 | — | — |

AA = Cocklebur, BB = Velvetleaf, CC = Black nightshade, DD = Barnyardgrass, EE = Large crabgrass, FF = Giant foxtail, GG = Corn, HH = Sorgo Table 28 shows that the herbicides of the present invention can selectively control a broad range of upland soil weeds without causing phytotoxicity on corn and sorgo. In contrast, it is shown that Compound F is poor in efficacy on grass weeds.

(e) Upland post-emergence treatment test 3

An upland post-emergence treatment test was carried out in the following manner with regard to Compound No. 15 (Example) and Compound (G) (Comparative Example).

Seeds of weeds such as velvetleaf, common ragweed, barnyardgrass and giant foxtail and seeds of corn and sorgo were sown in 1/5,000-are Wagner pots filled with upland soil, and covered with upland soil. The seeds were grown in a greenhouse, and at the stage of 3–4 leaves of these plants, a predetermined amount of the herbicide prepared in the above (1) was suspended in water and uniformly sprayed onto leaf and stalk portions at a rate of 2,000 l/ha. Then, the plants were grown in the greenhouse, and on the 30th day after the treatment, the herbicide was evaluated for herbicidal efficacy and phytotoxicity to the crops on the basis of the ratings shown in (2). Table 29 shows the results.

TABLE 29

| Com'd No. | Dosage (g/ha) | Herbicidal efficacy | | | | Phytotoxicity | |
|---|---|---|---|---|---|---|---|
| | | AA | BB | CC | DD | EE | FF |
| 15 | 50 | 5 | 5 | 5 | 5 | — | — |
| G | 50 | 5 | 2 | 1 | 0 | — | — |

AA = Velvetleaf, BB = Common ragweed, CC = Barnyardgrass, DD = Giant foxtail, EE = Corn, FF = Sorgo Table 29 shows that the herbicide of the present invention causes no phytotoxicity on corn and sorgo and further that it can selectively control main upland soil weeds at a low dosage. In contrast, it is shown that Compound G is poor in efficacy on common ragweed, barnyardgrass and giant foxtail which are mainly to be controlled in upland fields.

The cyclohexanedione derivative of the present invention can selectively control a broad range of upland soil weeds at a low dosage both in pre-emergence treatment and in post-emergence treatment without causing phytotoxicity on crops cultivated in upland fields such as corn.

What is claimed is:

1. Cyclohexanedione derivatives of the general formula $$\text{(I)}$$

wherein each of $R^1$ and $R^2$ is independently a hydrogen atom or a $C_1$–$C_4$ alkyl group, each of $R^3$ to $R^6$ is independently a hydrogen atom, a $C_1$–$C_4$ alkyl group, a $C_1$–$C_4$ haloalkyl group or a halogen atom, n is an integer of 0, 1 or 2, X is a $C_1$–$C_4$ alkyl group, a $C_1$–$C_4$ haloakyl group, a halogen atom, a $C_1$–$C_4$ alkoxy group, a $C_1$–$C_4$ haloalkoxy group, a $C_2$–$C_4$ alkoxyalkyl group, a $C_1$–$C_4$ alkylthio group, a $C_1$–$C_4$ haloalkylthio group, a $C_1$–$C_4$ alkylsulfinyl group or a $C_1$–$C_4$ alkylsulfonyl group, Y is a hydrogen atom, a $C_1$–$C_4$ alkyl group, $C_1$–$C_4$ haloalkyl group, a halogen atom, a $C_1$–$C_4$ alkoxy group, a $C_1$–$C_4$ haloalkoxy group or a $C_2$–$C_4$ alkoxyalkyl group, and Z is a group of $$\text{(a)} \quad \text{or} \quad \text{(b)}$$

in which each of $R^7$ and $R^8$ is independently a hydrogen atom, a halogen atom, a $C_1$–$C_4$ alkyl group, a $C_1$–$C_4$ alkoxy group, a $C_1$–$C_4$ alkylthio group or a group of $-NR^{10}R^{11}$, provided that when $R^7$ and/or $R^8$ are/is $C_1$–$C_4$ alkyl, $C_1$–$C_4$ alkoxy or $C_1$–$C_4$ alkylthio group (s), 1 to 9 hydrogen atoms may be substituted with 1 to 9 halogen atoms and that when the carbon number thereof is $C_2$–$C_4$, the group(s) may contain an unsaturated bond, each of $R^{10}$ and $R^{11}$ is a hydrogen atom, a $C_1$–$C_4$ alkyl group or a $C_1$–$C_4$ alkylcarbonyl group, further provided that when both $R^7$ and $R^8$ are $C_1$–$C_4$ alkyl groups, $C_1$–$C_4$ alkoxy groups or $C_1$–$C_4$ alkylthio groups, carbon atoms of $R^7$ and $R^8$ may bond to each other to form a 3- to 7-membered ring, provided that when both $R^7$ and $R^8$ are alkyl groups, compounds of the general formula (I) in which X is a $C_1$–$C_4$ alkyl group, a halogen atom or a haloalkyl group and all of $R^3$, $R^4$, $R^5$ and $R^6$ are hydrogen atoms are excluded, provided that when one of $R^7$ and $R^8$ is an alkoxy group and when the other is a hydrogen atom, compounds of the general formula (I) in which X is a $C_1$–$C_4$ alkyl group and all of $R^3$, $R^4$, $R^5$ and $R^6$ are hydrogen atoms when no hydrogen atom of the alkoxy group is replaced with halogen or when the alkoxy group contains no unsaturated bond are excluded, and $R^9$ is an oxygen atom, a sulfur atom or a $C_1$–$C_4$ alkoxyimino group, provided that when $R^9$ is $C_1$–$C_4$ alkoxyimino group, 1 to 9 hydrogen atoms thereof may be replaced with 1 to 9 halogen atoms and that when the carbon number is $C_2$–$C_4$, the $C_2$–$C_4$ alkoxyimino group may contain an unsaturated bond, and provided that compounds of the general formula (I) in which X is a $C_1$–$C_4$ alkyl group and all of $R^3$, $R^4$, $R^5$ and $R^6$ are hydrogen atoms when $R^9$ is an alkoxyimino group and when no hydrogen atom thereof is replaced with a halogen or the alkoxyimino group contains no unsaturated bond are excluded, or salts thereof.

2. Cyclohexanedione derivatives of the general formula (I-a1), $$\text{(I-a1)}$$

wherein each of $R^1$ and $R^2$ is independently a hydrogen atom or a $C_1$–$C_4$ alkyl group, each of $R^3$ to $R^6$ is independently a hydrogen atom, a $C_1$–$C_4$ alkyl group, a $C_1$–$C_4$ haloalkyl group or a halogen atom, n is 0, 1 or 2, X is a $C_1$–$C_4$ alkyl group, a $C_1$–$C_4$ haloalkyl group, a halogen atom, a $C_1$–$C_4$ alkoxy group, a $C_1$–$C_4$ haloalkoxy group, a $C_2$–$C_4$ alkoxyalkyl group, a $C_1$–$C_4$ alkylthio group, a $C_1$–$C_4$ haloalkylthio group, a $C_1$–$C_4$ alkylsulfinyl group or a $C_1$–$C_4$ alkylsulfonyl group, Y is a hydrogen atom, a $C_1$–$C_4$ alkyl group, a $C_1$–$C_4$ haloalkyl group, a halogen atom, a $C_1$–$C_4$ alkoxy group, a $C_1$–$C_4$ haloalkoxy group or a $C_2$–$C_4$ alkoxyalkyl group, and $R^{12}$ is a $C_1$–$C_4$ alkyl group or a $C_1$–$C_4$ haloalkyl group, provided that compounds of the general formula (I-a1) in which X is a $C_1$–$C_4$ alkyl group and all of $R^3$, $R^4$, $R^5$ and $R^6$ are hydrogen atoms when $R^{12}$ is a $C_1$–$C_4$ alkyl group are excluded, or salts thereof.

3. Cyclohexanedione derivatives of the general formula (I-a2), $$\text{(I-a2)}$$

wherein each of $R^1$ and $R^2$ is independently a hydrogen atom or a $C_1$–$C_4$ alkyl group, each of $R^3$ to $R^6$ is independently a hydrogen atom, a $C_1$–$C_4$ alkyl group, a $C_1$–$C_4$ haloalkyl group or a halogen atom, $R^{13}$ is a $C_1$–$C_4$ alkyl group, n is 0, 1 or 2, $X^1$ is a $C_1$–$C_4$ haloalkyl group, a halogen atom, a $C_1$–$C_4$ alkoxy group, a $C_1$–$C_4$ haloalkoxy group, a $C_2$–$C_4$ alkoxyalkyl group, a $C_1$–$C_4$ alkylthio group, a $C_1$–$C_4$ haloalkylthio group, a $C_1$–$C_4$ alkylsulfinyl group or a $C_1$–$C_4$ alkylsulfonyl group, and Y is a hydrogen atom, a $C_1$–$C_4$ alkyl group, a $C_1$–$C_4$ haloalkyl group, a halogen atom, a $C_1$–$C_4$ alkoxy group, a $C_1$–$C_4$ haloalkoxy group or a $C_2$–$C_4$ alkoxyalkyl group, or salts thereof.

4. Cyclohexanedione derivatives of the general formula (I-a3),

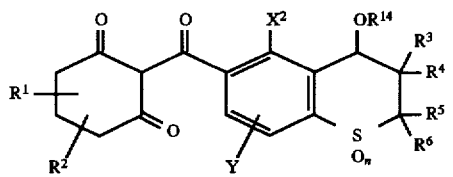

wherein each of $R^1$ and $R^2$ is independently a hydrogen atom or a $C_1$-$C_4$ alkyl group, each of $R^3$ to $R^6$ is independently a hydrogen atom, a $C_1$-$C_4$ alkyl group, a $C_1$-$C_4$ haloalkyl group or a halogen atom, $R^{14}$ is a $C_1$-$C_4$ haloalkyl group, n is 0, 1 or 2, $X^2$ is a $C_1$-$C_4$ alkyl group, a $C_1$-$C_4$ haloalkyl group, a halogen atom, a $C_1$-$C_4$ alkoxy group, a $C_1$-$C_4$ haloalkoxy group, a $C_2$-$C_4$ alkoxyalkyl group, a $C_1$-$C_4$ alkylthio group, a $C_1$-$C_4$ haloalkylthio group, a $C_1$-$C_4$ alkylsulfinyl group or a $C_1$-$C_4$ alkylsulfonyl group, and Y is a hydrogen atom, a $C_1$-$C_4$ alkyl group, a $C_1$-$C_4$ haloalkyl group, a halogen atom, a $C_1$-$C_4$ alkoxy group, a $C_1$-$C_4$ haloalkoxy group or a $C_2$-$C_4$ alkoxyalkyl group, or salts thereof.

5. Cyclohexanedione derivatives of the general formula (I-b1),

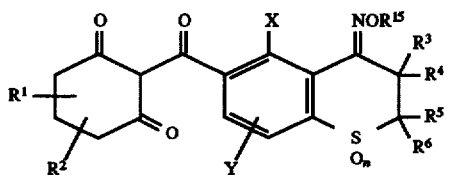

wherein each of $R^1$ and $R^2$ is independently a hydrogen atom or a $C_1$-$C_4$ alkyl group, each of $R^3$ to $R^6$ is independently a hydrogen atom, a $C_1$-$C_4$ alkyl group, a $C_1$-$C_4$ haloalkyl group or a halogen atom, n is 0, 1 or 2, X is a $C_1$-$C_4$ alkyl group, a $C_1$-$C_4$ haloalkyl group, a halogen atom, a $C_1$-$C_4$ alkoxy group, a $C_1$-$C_4$ haloalkoxy group, a $C_2$-$C_4$ alkoxyalkyl group, a $C_1$-$C_4$ alkylthio group, a $C_1$-$C_4$ haloalkylthio group, a $C_1$-$C_4$ alkylsulfinyl group or a $C_1$-$C_4$ alkylsulfonyl group, Y is a hydrogen atom, a $C_1$-$C_4$ alkyl group, a $C_1$-$C_4$ haloalkyl group, a halogen atom, a $C_1$-$C_4$ alkoxy group, a $C_1$-$C_4$ haloalkoxy group or a $C_2$-$C_4$ alkoxyalkyl group, and $R^{15}$ is a $C_1$-$C_4$ alkyl group or a $C_2$-$C_4$ alkenyl group, provided that compounds of the general formula (I-b1) in which X is a $C_1$-$C_4$ alkyl group and all of $R^3$, $R^4$, $R^5$ and $R^6$ are hydrogen atoms when $R^{15}$ is a $C_1$-$C_4$ alkyl group are excluded, or salts thereof.

6. Cyclohexanedione derivatives of the general formula (I-b2),

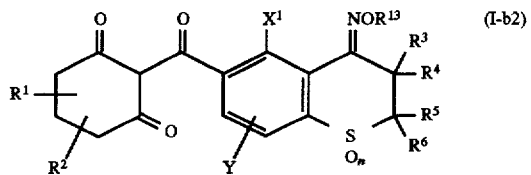

wherein each of $R^1$ and $R^2$ is independently a hydrogen atom or a $C_1$-$C_4$ alkyl group, each of $R^3$ to $R^6$ is independently a hydrogen atom, a $C_1$-$C_4$ alkyl group, a $C_1$-$C_4$ haloalkyl group or a halogen atom, $R^{13}$ is a $C_1$-$C_4$ alkyl group, n is 0, 1 or 2, $X^1$ is a $C_1$-$C_4$ haloalkyl group, a halogen atom, a $C_1$-$C_4$ alkoxy group, a $C_1$-$C_4$ haloalkoxy group, a $C_2$-$C_4$ alkoxyalkyl group, a $C_1$-$C_4$ alkylthio group, a $C_1$-$C_4$ haloalkylthio group, a $C_1$-$C_4$ alkylsulfinyl group or a $C_1$-$C_4$ alkylsulfonyl group, and Y is a hydrogen atom, a $C_1$-$C_4$ alkyl group, a $C_1$-$C_4$ haloalkyl group, a halogen atom, a $C_1$-$C_4$ alkoxy group, a $C_1$-$C_4$ haloalkoxy group or a $C_2$-$C_4$ alkoxyalkyl group, or salts thereof.

7. Cyclohexanedione derivatives of the general formula (I-c),

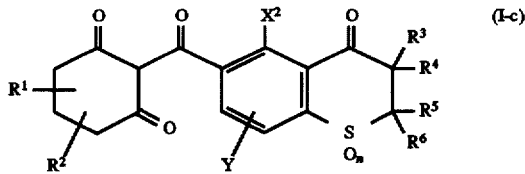

wherein each of $R^1$ and $R^2$ is independently a hydrogen atom or a $C_1$-$C_4$ alkyl group, each of $R^3$ to $R^6$ is independently a hydrogen atom, a $C_1$-$C_4$ alkyl group, a $C_1$-$C_4$ haloalkyl group or a halogen atom, n is 0, 1 or 2, $X^2$ is a $C_1$-$C_4$ alkyl group, a $C_1$-$C_4$ haloalkyl group, a halogen atom, a $C_1$-$C_4$ alkoxy group, a $C_1$-$C_4$ haloalkoxy group, a $C_2$-$C_4$ alkoxyalkyl group, a $C_1$-$C_4$ alkylthio group, a $C_1$-$C_4$ haloalkylthio group, a $C_1$-$C_4$ alkylsulfinyl group or a $C_1$-$C_4$ alkylsulfonyl group, and Y is a hydrogen atom, a $C_1$-$C_4$ alkyl group, a $C_1$-$C_4$ haloalkyl group, a halogen atom, a $C_1$-$C_4$ alkoxy group, a $C_1$-$C_4$ haloalkoxy group or a $C_2$-$C_4$ alkoxyalkyl group, or salts thereof.

8. The cyclohexanedione derivatives of claim 1, wherein each of $R^3$, $R^4$, $R^5$ and $R^6$ is independently a hydrogen atom or methyl.

9. The cyclohexanedione derivatives of claim 1, wherein Y is substituted on the 8-position of a thiochroman ring.

10. The cyclohexanedione derivatives of claim 1, wherein n is 0 or 2.

11. Herbicides containing, as active ingredients, the cyclohexanedione derivatives or the salts thereof recited in claim 1.

* * * * *